US008939899B2

(12) United States Patent
Kitagawa et al.

(10) Patent No.: US 8,939,899 B2
(45) Date of Patent: Jan. 27, 2015

(54) ENDOSCOPE BENDING PORTION AND MANUFACTURING METHOD OF BENDING TUBE

(75) Inventors: Hideya Kitagawa, Hachioji (JP); Shunichi Imai, Okaya (JP)

(73) Assignees: Olympus Corporation, Tokyo (JP); Olympus Medical Systems Corp., Tokyo (JP)

( * ) Notice: Subject to any disclaimer, the term of this patent is extended or adjusted under 35 U.S.C. 154(b) by 713 days.

(21) Appl. No.: 13/220,316

(22) Filed: Aug. 29, 2011

(65) Prior Publication Data
US 2011/0313251 A1 Dec. 22, 2011

Related U.S. Application Data

(63) Continuation of application No. PCT/JP2010/056353, filed on Apr. 8, 2010.

(30) Foreign Application Priority Data

Apr. 21, 2009 (JP) ................. 2009-103163

(51) Int. Cl.
*A61B 1/00* (2006.01)
*A61B 1/005* (2006.01)
*G02B 23/24* (2006.01)

(52) U.S. Cl.
CPC .......... *A61B 1/0055* (2013.01); *G02B 23/2476* (2013.01)
USPC ............................. 600/142; 600/139; 600/141

(58) Field of Classification Search
USPC .................................. 600/139–144
See application file for complete search history.

(56) References Cited

U.S. PATENT DOCUMENTS

| 4,834,069 | A | 5/1989 | Umeda |
| 5,178,129 | A * | 1/1993 | Chikama et al. .............. 600/142 |
| 2007/0225565 | A1 | 9/2007 | Ogino |
| 2009/0012364 | A1 | 1/2009 | Kitagawa et al. |

FOREIGN PATENT DOCUMENTS

| JP | 55-164003 U | 11/1980 |
| JP | 61-21042 Y2 | 6/1986 |

(Continued)

OTHER PUBLICATIONS

International Search Report (ISR) dated Jun. 22, 2010 (and English translation thereof) in counterpart International Application No. PCT/JP2010/056353.

(Continued)

*Primary Examiner* — Matthew J Kasztejna
(74) *Attorney, Agent, or Firm* — Holtz, Holtz, Goodman & Chick PC

(57) ABSTRACT

Each of the first hinge portions includes a first central planar portion, and first both-sides planar portion, and each of second hinge portions includes a second central planar portion, and second both-sides planar portion which is arranged on the same plane as the first both-sides planar portion. At least one of each first hinge portion and each second hinge portion includes/include an axial step portion which is provided between the first central planar portion and the first both-sides planar portion and/or between the second central planar portion and the second both-sides planar portion over the entire length of the nodal ring in the longitudinal direction and allows/allow the first central planar portion to be arranged to an outer peripheral side than the second central planar portion by a distance corresponding to a wall thickness of the nodal ring.

6 Claims, 26 Drawing Sheets

(56) References Cited

FOREIGN PATENT DOCUMENTS

| | | |
|---|---|---|
| JP | 64-39701 U | 3/1989 |
| JP | 2-82936 A | 3/1990 |
| JP | 2007-159636 A | 6/2007 |
| JP | 2007-185314 A | 7/2007 |
| JP | 2007-252448 A | 10/2007 |

OTHER PUBLICATIONS

Japanese Office Action dated Dec. 4, 2012 (and English translation thereof) in counterpart Japanese Application No. 2009-103163.
International Preliminary Report on Patentability (IPRP) dated Dec. 1, 2011 (in English) in parent International Application No. PCT/JP2010/056353.

* cited by examiner

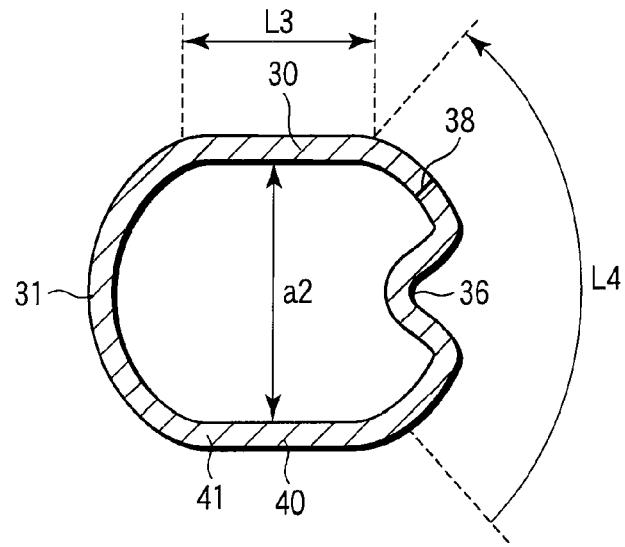
F I G. 5
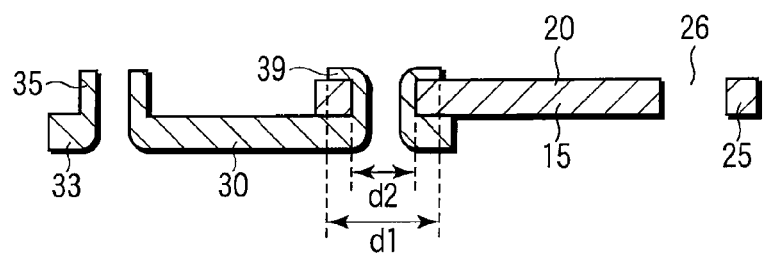
F I G. 6
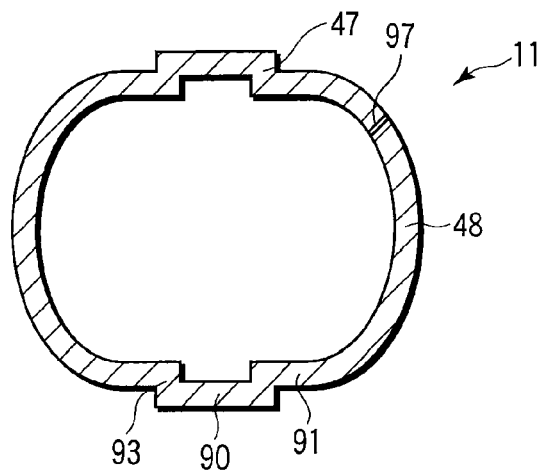
F I G. 7

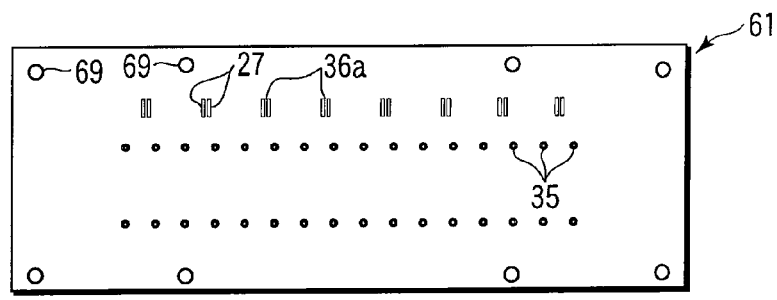
F I G. 15
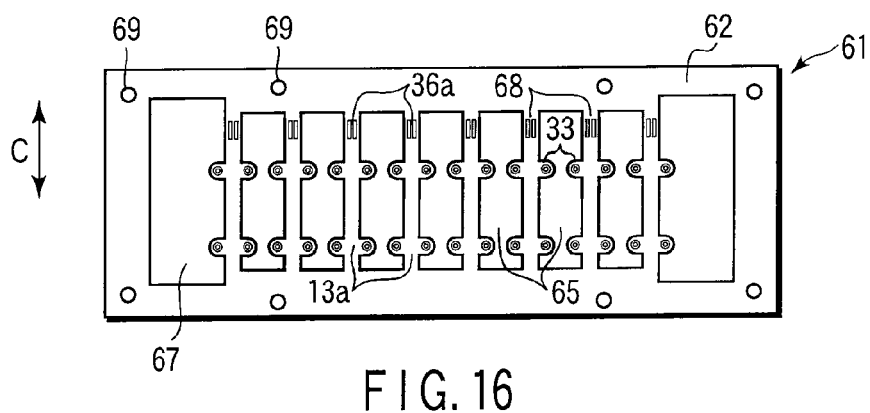
F I G. 16
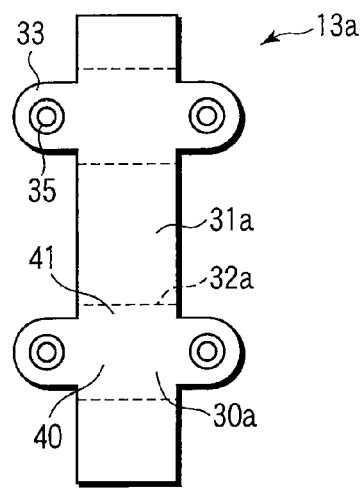
F I G. 17

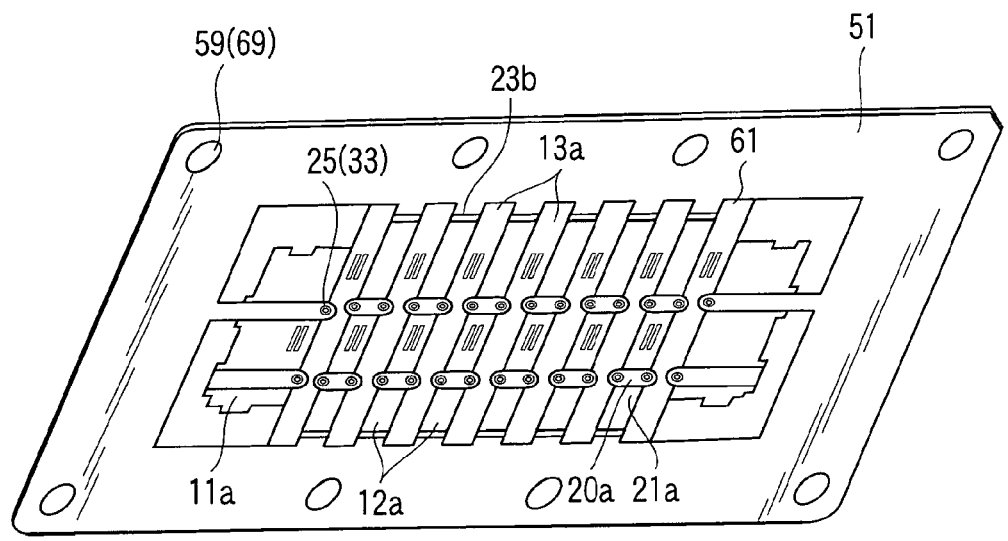
F I G. 18A
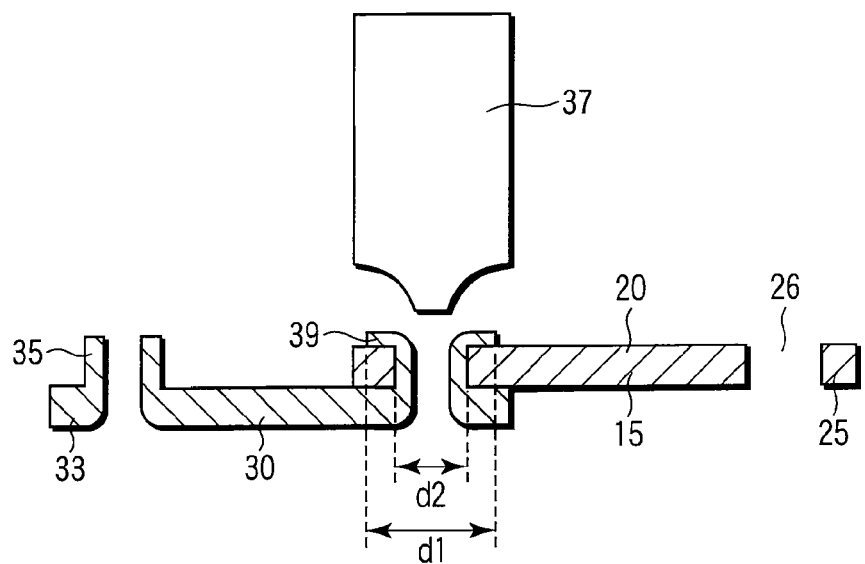
F I G. 18B

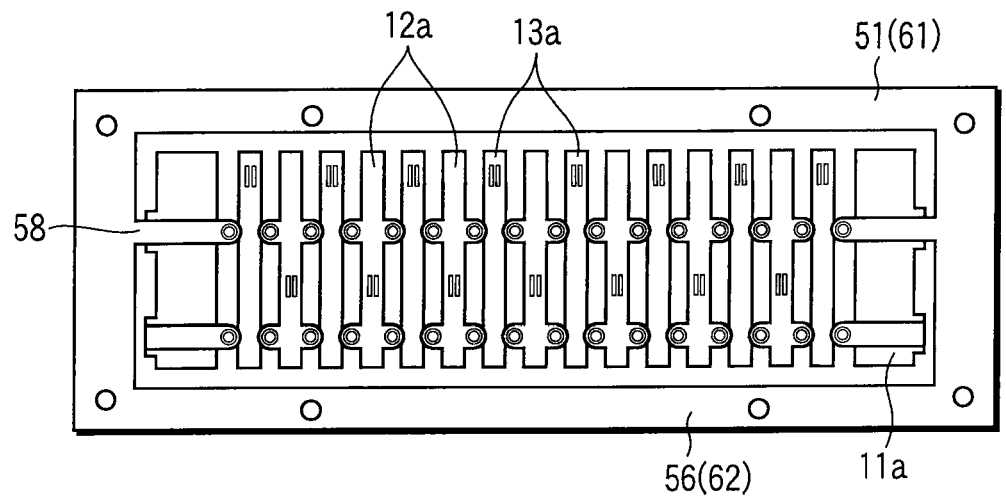
F I G. 19
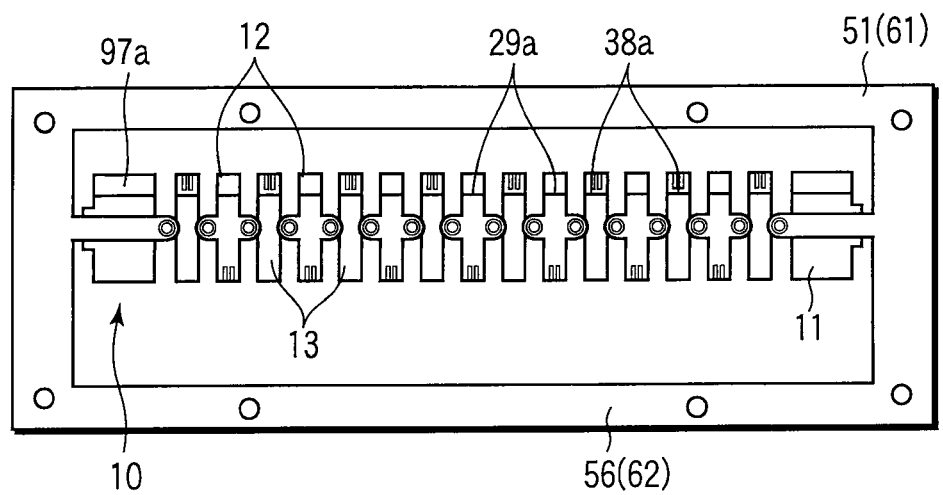
F I G. 20

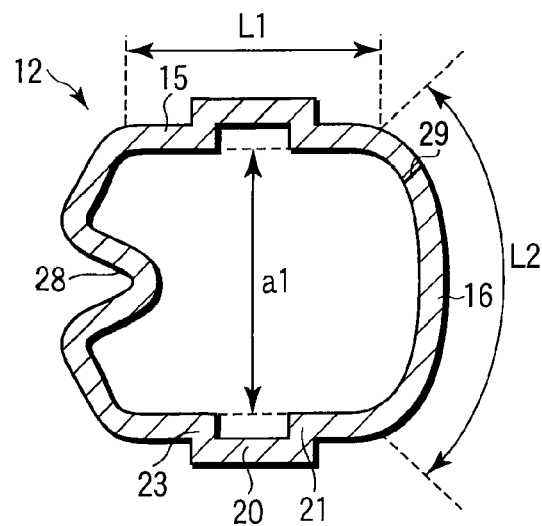
F I G. 22A
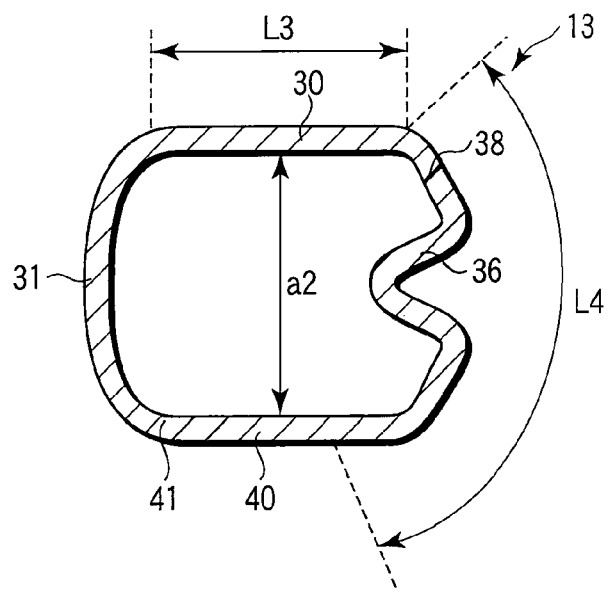
F I G. 22B

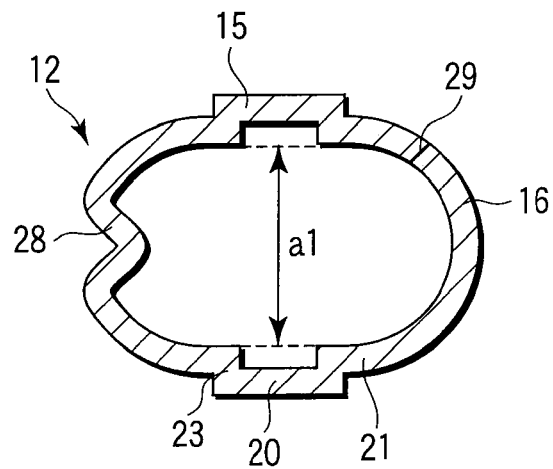
F I G. 23A
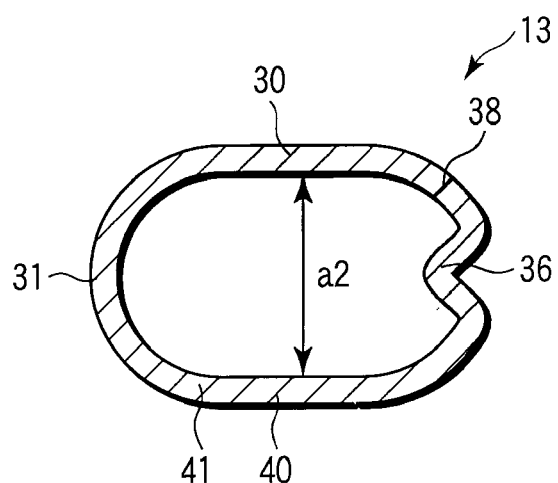
F I G. 23B

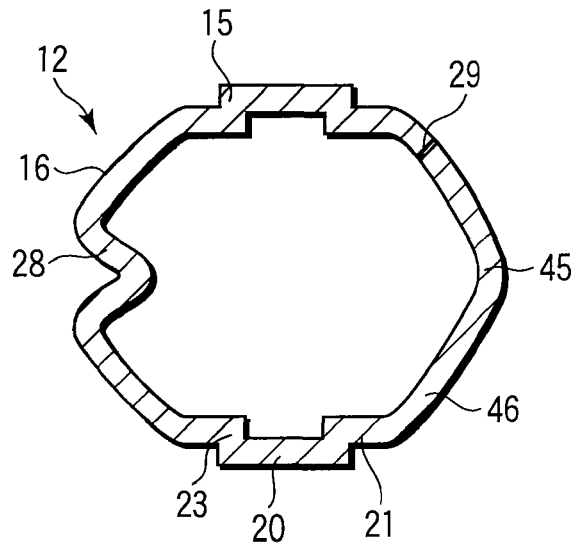
F I G. 25A
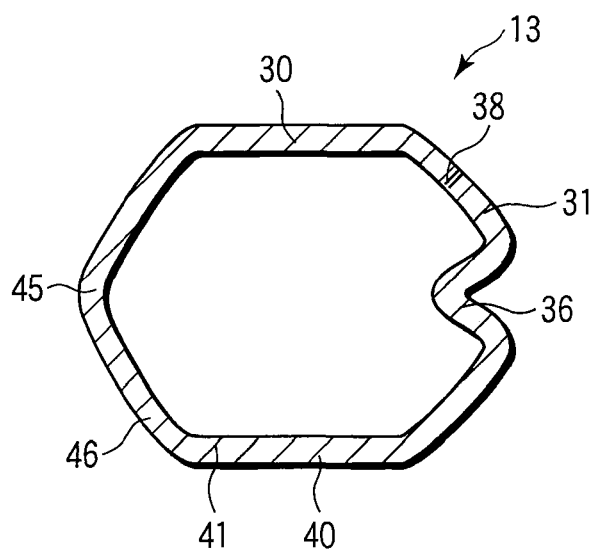
F I G. 25B

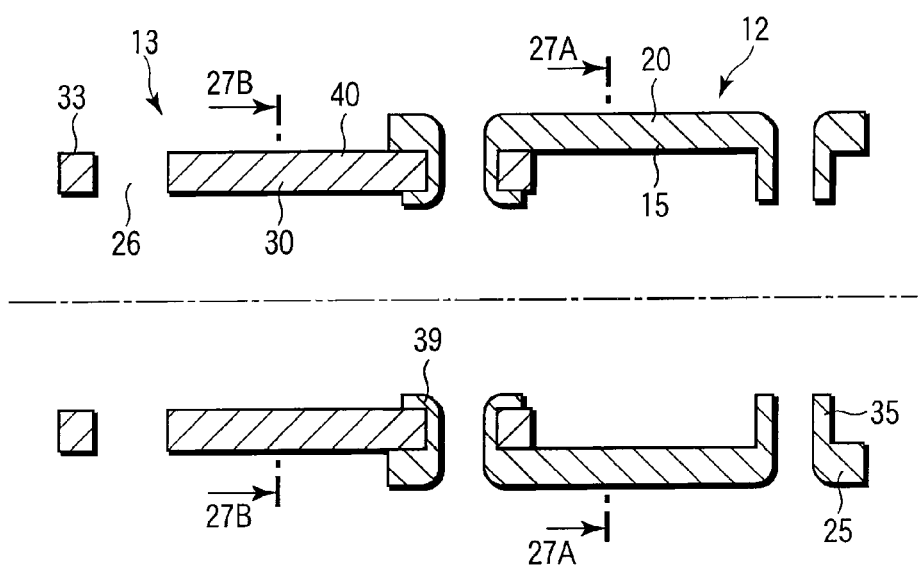
F I G. 26

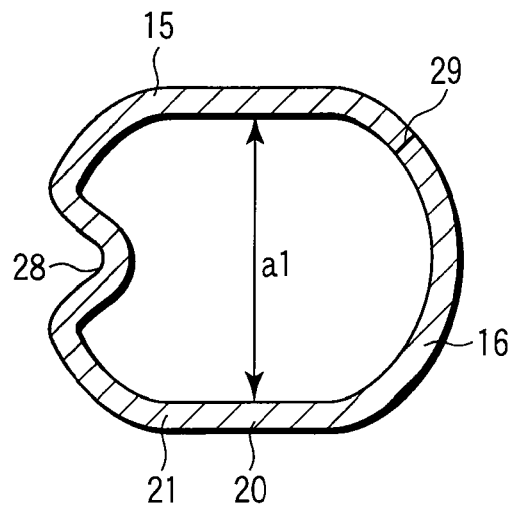
F I G. 29A
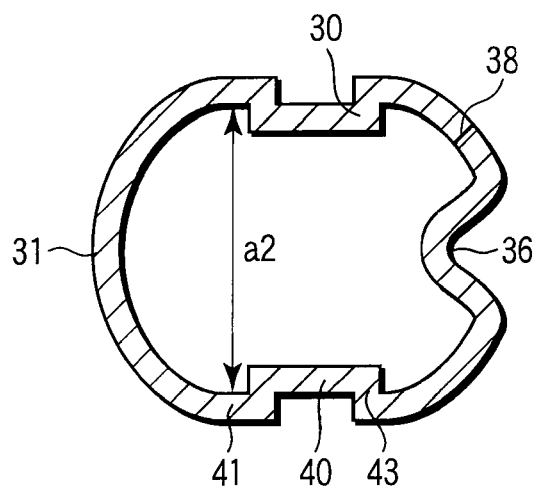
F I G. 29B

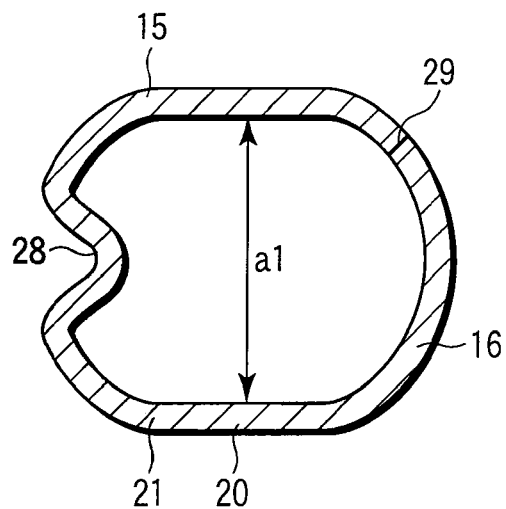
F I G. 31A
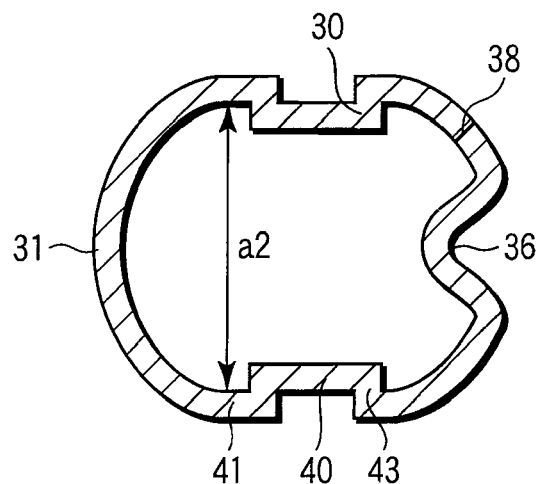
F I G. 31B

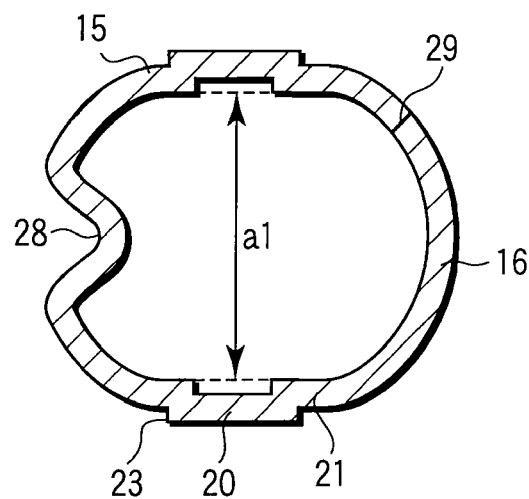
F I G. 33A
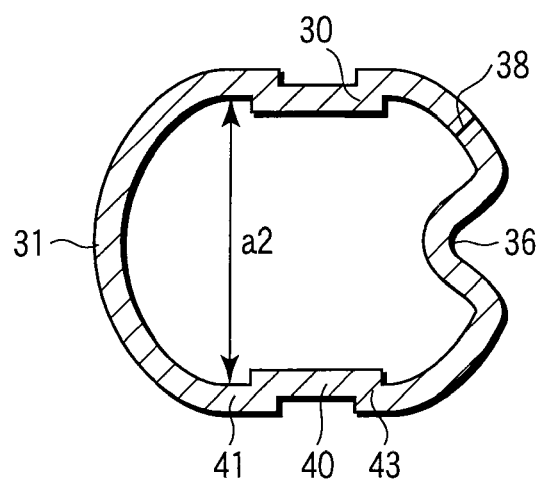
F I G. 33B

ENDOSCOPE BENDING PORTION AND MANUFACTURING METHOD OF BENDING TUBE

CROSS REFERENCE TO RELATED APPLICATIONS

This application is a Continuation Application of PCT Application No. PCT/JP2010/056353, filed Apr. 8, 2010 and based upon and claiming the benefit of priority from prior Japanese Patent Application No. 2009-103163, filed Apr. 21, 2009, the entire contents of all of which are incorporated herein by reference.

BACKGROUND OF THE INVENTION

1. Field of the Invention

The present invention relates to an endoscope bending portion and a manufacturing method of a bending tube which forms the endoscope bending portion.

2. Description of the Related Art

In general, an endoscope includes an elongated insertion portion configured to be inserted into a body cavity and an operation portion connected to a proximal end side of the insertion portion. The insertion portion includes an elongated flexible tube having flexibility, a bending portion that is connected to a distal end side of the flexible tube and operated to bend, and a distal-end hard portion connected to a distal end side of the bending portion. The bending portion includes a bending tube, and an envelope tube made of, e.g., a rubber material and coating an outer peripheral surface of the bending tube. The bending tube is formed by arranging nodal rings along the longitudinal direction of the endoscope bending portion in line and coupling these nodal rings to allow each of them to rotate. A front-end nodal ring which is the nodal ring closest to the distal-end hard portion is coupled with the distal-end hard portion, and a rear-end nodal ring which is the nodal ring closest to the operation portion is coupled with the flexible tube.

Japanese Examined Utility Mode Application Publication No. Sho 61-21042 (1986) discloses an endoscope bending portion having a configuration that strip-like nodal ring preliminary bodies are formed into circular shapes to provide nodal rings and the nodal rings are coupled with each other to allow each of them to rotate.

JP-A 2007-185314 (KOKAI) discloses a manufacturing method of a bending tube in which a plate-like member is pressed to continuously form strip-like nodal ring preliminary bodies, the nodal ring preliminary bodies are coupled with each other, and then the nodal ring preliminary bodies are collectively formed into circular shapes. In this manufacturing method of the bending tube, the strip-like nodal ring preliminary bodies are first continuously formed in the plate-like member by press work. Each nodal ring preliminary body includes a pair of first tongue piece portions provided on one end side in the longitudinal direction and arranged to be apart from each other at 180° in the circumferential direction of the nodal ring after formed into the circular shape, and second tongue piece portions provided on the other end side in the longitudinal direction and arranged to be apart from each first tongue piece portion at substantially 90° in the circumferential direction of the nodal ring after formed into the circular shape. Through hole is formed in each of the first tongue portions, and a protruding portion is formed on each of the second tongue piece portions by burring processing.

Further, the nodal ring preliminary bodies are coupled by sequentially coupling the through hole in each of the first tongue portions of each of the circular piece preliminary bodies with the protruding portion of a corresponding second tongue portion of an adjacent nodal ring preliminary body. Furthermore, the nodal ring preliminary bodies are formed into the circular shapes, and both ends of each nodal ring preliminary body are bonded to form a nodal ring. In this manner, the bending tube is formed.

BRIEF SUMMARY OF THE INVENTION

According to one aspect of the invention, an endoscope bending portion includes that a bending tube in which two types of nodal rings that are first nodal rings and second nodal rings are alternately coupled with each other in a longitudinal direction to allow each of them to rotate, wherein each of the first nodal rings includes a pair of first hinge portions each of which includes a first central planar portion including a first coupling portion as a coupling portion with respect to the corresponding second nodal, and first both-sides planar portion which is provided on both sides of the first central planar portion in a circumferential direction, the first hinge portions being arranged to be symmetrical about a longitudinal axis with respect to each other, each of the second nodal rings includes a pair of second hinge portions each of which includes a second central planar portion including a second coupling portion coupled with the first coupling portion of the corresponding first nodal ring, and second both-sides planar portion which is provided on both sides of the second central planar portion in the circumferential direction and arranged on the same plane as the first both-sides planar portion of each of the first hinge portion, the second hinge portions being arranged to be symmetrical about the longitudinal axis with respect to each other, and at least one of each first hinge portion of each of the first nodal rings and each second hinge portion of each of the second nodal rings includes/include an axial step portion which is provided between the first central planar portion and the first both-sides planar portion over the entire length of the first nodal ring in the longitudinal direction and/or between the second central planar portion and the second both-sides planar portion over the entire length of the second nodal ring in the longitudinal direction and allows/allow the first central planar portion to be arranged to an outer peripheral side of the bending tube than the second central planar portion by a distance corresponding to a wall thickness of the nodal ring.

According to one another aspect of the invention, a manufacturing method of a bending tube in which two types of nodal rings that are first nodal rings and second nodal rings are alternately coupled with each other in a longitudinal direction to allow each of them to rotate, includes that forming in a first plate-like member a predetermined number of first nodal-ring preliminary bodies obtained by expanding the first nodal rings into a strip-like shape in a state that both ends or one end of each first nodal ring preliminary body is coupled with an edge of the first plate-like member through a first edge crosspiece portion in the circumferential direction while providing gaps between the first nodal ring preliminary bodies where second nodal ring preliminary bodies obtained by expanding the second nodal rings into a strip-like shape are arranged; forming in a second plate-like member different from the first plate-like member the second nodal ring preliminary bodies in a state that both ends or one end of each second nodal ring preliminary body is coupled with an edge of the second plate-like member through a second edge crosspiece portion in the circumferential direction while providing gaps between the second nodal ring preliminary bodies where the first nodal ring preliminary bodies are arranged; forming a protruding portion on one of a first coupling portion provided to each first nodal ring preliminary body and a second coupling portion provided to each second nodal ring preliminary body by burring processing; forming a through hole, which engages with the protruding portion, in the other of each first coupling portion and each second coupling portion; engaging the protruding portions with the through holes and coupling the first nodal ring preliminary bodies with the second nodal ring preliminary bodies in a state that the first plate-like member and the second plate-like member overlap each other; disconnecting the first nodal ring preliminary bodies from the edge of the first plate-like member at the first edge crosspiece portion and disconnecting the second nodal ring preliminary bodies from the edge of the second plate-like member at the second edge crosspiece portion; and forming the first nodal ring preliminary bodies and the second nodal ring preliminary bodies into a circular shapes by bending processing and joining and connecting part or entire of both ends of each first nodal ring preliminary body and each second nodal ring preliminary body in the circumferential direction.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a cross-sectional view taken along a line V-V in FIG. 2;

FIG. 6 is a cross-sectional view taken along a line VI-VI in FIG. 3;

FIG. 7 is a cross-sectional view taken along a line VII-VII in FIG. 2;

FIG. 15 is a plan view showing the second plate-like member according to the first embodiment in a state after performing a fifth hole drilling;

FIG. 16 is a plan view showing the second plate-like member according to the first embodiment in a state after performing a sixth hole drilling;

FIG. 17 is a plan view showing a second nodal ring preliminary body according to the first embodiment in a state after performing the sixth hole drilling;

FIG. 18A is a perspective view showing a bending tube according to the first embodiment in a state after performing an overlapping and a burring expanding;

FIG. 18B is a cross-sectional view showing a coupling portion of a first nodal ring and a second nodal ring according to the first embodiment in a state at the time of the burring expanding;

FIG. 19 is a plan view showing the bending tube according to the first embodiment in a state after performing an edge crosspiece portion cutting;

FIG. 20 is a plan view showing the bending tube according to the first embodiment in a state after performing a bending;

FIG. 22A is a cross-sectional view showing a first nodal ring according to a second modification of the first embodiment;

FIG. 22B is a cross-sectional view showing a second nodal ring according to the second modification of the first embodiment;

FIG. 23A is a cross-sectional view showing a first nodal ring according to a third modification of the first embodiment;

FIG. 23B is a cross-sectional view showing a second nodal ring according to the third modification of the first embodiment;

FIG. 25A is a cross-sectional view showing a first nodal ring according to a fifth modification of the first embodiment;

FIG. 25B is a cross-sectional view showing a second nodal ring according to the fifth modification of the first embodiment;

FIG. 26 is a cross-sectional view showing a first nodal ring and a second nodal ring according to a sixth modification of the first embodiment in a coupled state;

FIG. 29A is a cross-sectional view taken along a line 29A-29A in FIG. 28;

FIG. 29B is a cross-sectional view taken along a line 29B-29B in FIG. 28;

FIG. 31A is a cross-sectional view taken along a line 31A-31A in FIG. 30;

FIG. 31B is a cross-sectional view taken along a line 31B-31B in FIG. 30;

FIG. 33A is a cross-sectional view taken along a line 33A-33A in FIG. 32;

FIG. 33B is a cross-sectional view taken along a line 33B-33B in FIG. 32;

DETAILED DESCRIPTION OF THE INVENTION

A first embodiment according to the present invention will now be described hereinafter with reference to FIG. 1 to FIG. 20.

Figure 1:
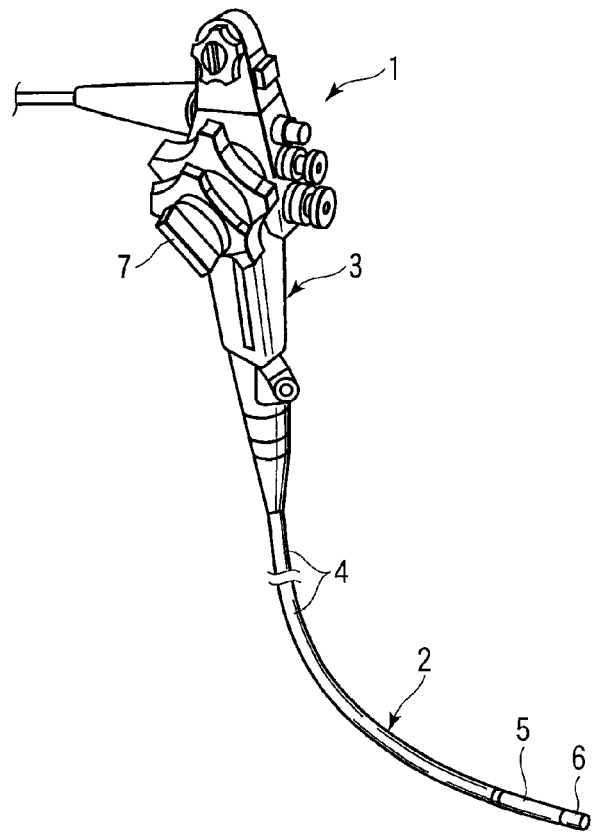
FIG. 1 is a perspective view showing an endoscope according to a first embodiment of the present invention.

FIG. 1 is a view showing an overall configuration of an endoscope 1. The endoscope 1 includes an elongated insertion portion 2 configured to be inserted into a body cavity, and an operation portion 3 connected to a proximal end side of the insertion portion 2. The insertion portion 2 includes an elongated flexible tube 4 having flexibility, a bending portion 5 connected to a distal end side of the flexible tube 4, and a distal-end hard portion 6 connected to a distal end side of the bending portion 5. An operation knob 7 configured to operate the bending portion 5 to bend and others are provided to the operation portion 3.

The bending portion 5 includes a bending tube 10 and a soft envelope tube (not shown) made of, e.g., a rubber material which coats an outer peripheral surface of the bending tube 10.

Figure 2:
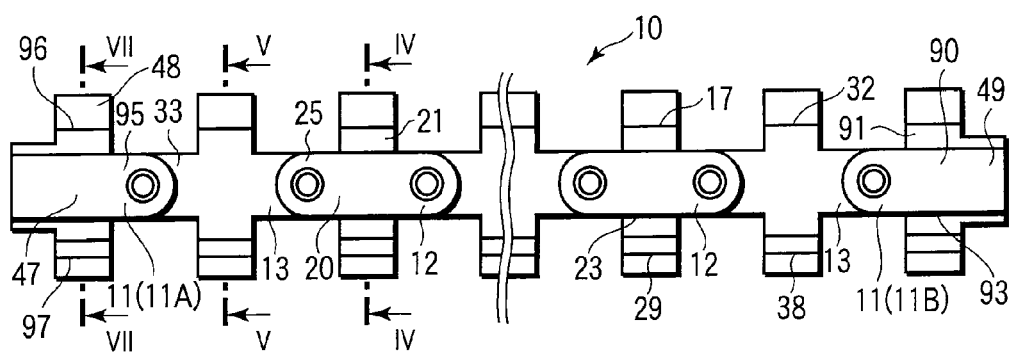
FIG. 2 is a plan view showing a bending tube according to the first embodiment.

FIG. 2 is a view showing a configuration of the bending tube 10. As shown in FIG. 2, in the bending tube 10, both-end nodal rings 11 constituted of a front-end nodal ring 11A coupled with the distal-end hard portion 6 and a rear-end nodal ring 11B coupled with the flexible tube 4 are provided. Two types of substantially circular nodal rings 12 and 13 (which will be referred to as first nodal rings 12 and second nodal rings 13 hereinafter) are alternately aligned in a longitudinal direction of the insertion portion 2 between the both-end nodal rings 11. The first nodal ring 12 and the second nodal ring 13 are coupled with each other to allow each of them to rotate.

Figure 3:
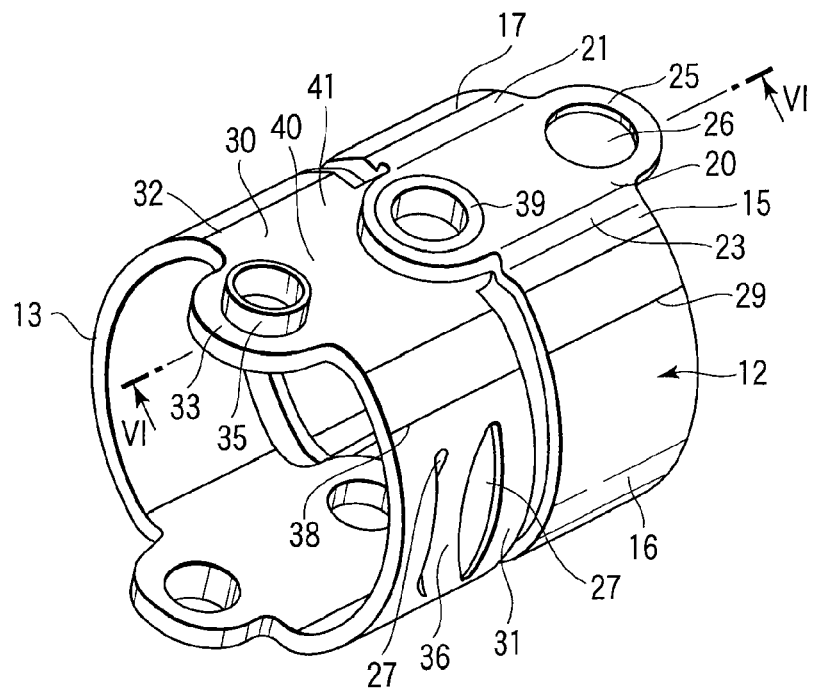
FIG. 3 is a perspective view showing a first nodal ring and a second nodal ring according to the first embodiment in a coupled state.

FIG. 3 is a view showing the first nodal ring 12 and the second nodal ring 13 in a coupled state. As shown in FIG. 3, the first nodal ring 12 includes a pair of planar first hinge portions 15 symmetrically provided about a central axis (an axis in the longitudinal direction) with respect to each other, and a pair of first circumferential wall portions 16 each of which is provided between the first hinge portions 15 and each of which has a cylindrical surface shape. A first ridge line 17 is formed between the first hinge portion 15 and the first circumferential wall portion 16.

Figure 4:
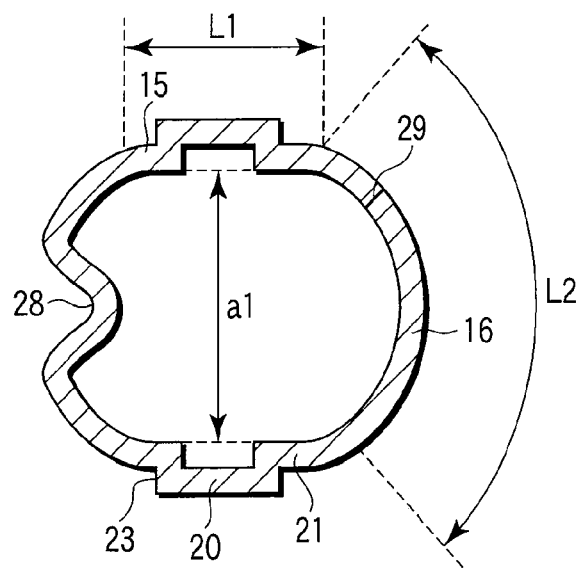
FIG. 4 is a cross-sectional view taken along a line IV-IV in FIG. 2.

FIG. 4 is a cross-sectional view taken along a line IV-IV in FIG. 2. As shown in FIG. 3 and FIG. 4, the first hinge portion 15 has a length L1 in the circumferential direction of the first nodal ring 12. The first hinge portion 15 includes a substantially elliptical first central planar portion 20, and a first both-sides planar portion 21 provided on both sides of the first central planar portion 20 in the circumferential direction of the first nodal ring 12 (bending tube 10). Axial step portions 23 are formed between the first central planar portion 20 and the first both-sides planar portion 21 over the entire length of the first nodal ring 12 in the axial direction (the longitudinal direction). When the axial step portions 23 are provided, the first central planar portion 20 is arranged to the outer peripheral side than the first both-sides planar portion 21 by a distance corresponding to a wall thickness of the first nodal ring 12. The first both-sides planar portions 21 each of which is provided to the corresponding first hinge portion 15 are apart from each other by a distance a1. As shown in FIG. 3, first tongue piece portions 25 which are first coupling portions are provided at both end portions of each first central planar portion 20 in the axial direction (the longitudinal direction) of the first nodal ring 12. A through hole 26 is formed at a central part of the first tongue piece portion 25.

As shown in FIG. 3 and FIG. 4, the first circumferential wall portion 16 is formed into a cylindrical surface shape and has a circumferential length L2 which is a length along the circumferential direction of the cylindrical surface. A first wire receiver 28 is provided in one of the pair of first circumferential wall portions 16. The first wire receiver 28 is formed by forming two slits 27 in the first circumferential wall portion 16 along the circumferential direction and protruding a strip-like portion between the two slits 27 in a C-like shape toward the inside in a radial direction. The first wire receiver 28 is arranged to be apart from each first central planar portion 20 at 90° in the circumferential direction of the first nodal ring 12. Here, the circumferential length L2 is a length which does not include the protruding portion of the first wire receiver 28.

It is to be noted that the first nodal ring 12 is formed by bringing both end surfaces of a first nodal ring preliminary body 12a into contact with each other and joining and connecting a part or entire of the contacted portions as will be described later. As a result, a first joint portion 29 is formed in the first nodal ring 12 along the axial direction (the longitudinal direction) of the first nodal ring 12.

As show in FIG. 3, the second nodal ring 13 includes a pair of second hinge portions 30 symmetrically provided about the central axis (the axis in the longitudinal direction) with respect to each other, and a pair of second circumferential wall portions 31 each of which is provided between the second hinge portions 30. A second ridge line 32 is formed between second hinge portion 30 and second circumferential wall portion 31. A wall thickness of the second nodal ring 13 is substantially equal to a wall thickness of the first nodal ring 12.

FIG. 5 is a cross-sectional view taken along a line V-V in FIG. 2. As shown in FIG. 3 and FIG. 5, the second hinge portion 30 includes a substantially elliptical second central planar portion 40, and a second both-sides planar portion 41 provided on both sides of the second central planar portion 40 in the circumferential direction of the second nodal ring 13 (the bending tube 10). In this embodiment, the second central planar portion 40 and the second both-sides planar portion 41 are formed on the same plane. Therefore, the second hinge portions 30 are formed into a planar shape and apart from each other by a distance a2 (the second both-sides planar portions 41 are apart from each other by the distance a2). A length L3 of the second hinge portion 30 in the circumferential direction of the second nodal ring 13 is equal to a length L1 of the first hinge portion 15 in the circumferential direction. As shown in FIG. 3, second tongue piece portions 33 which are second coupling portions are provided at both end portions of each second hinge portion 30 in the axial direction (the longitudinal direction) of each second nodal ring 13. A protruding portion 35 protruding toward an outer peripheral side of the second nodal ring 13 is formed at a central part of the second tongue piece portion 33. The protruding portion 35 is formed by, e.g., a burring processing.

As shown in FIG. 3 and FIG. 5, each second circumferential wall portion 31 is formed into a cylindrical surface shape. A circumferential length L4 which is a length along the circumferential direction of the cylindrical surface of the second circumferential wall portion 31 is equal to a circumferential length L2 of the first circumferential wall portion 16. As a result, a first circumferential dimension S1 which is a sum of the length L1 of the pair of first hinge portions 15 in the circumferential direction of the first nodal ring 12 and the circumferential length L2 of the pair of first circumferential wall portions 16 (S1=2L1+2L2) is equal to a second circumferential dimension S2 which is a sum of the length L3 of the pair of second hinge portions 30 in the circumferential direction of the second nodal ring 13 and the circumferential length L4 of the pair of second circumferential wall portions 31 (S2=2L3+2L4). Further, a cross-sectional shape of the second circumferential wall portion 31 perpendicular to the axial direction of the bending tube 10 (a second cross-sectional shape) is congruent with a cross-sectional shape of the first circumferential wall portion 16 perpendicular to the axial direction of the bending tube 10 (a first cross-sectional shape). When such a configuration is adopted, the distance a1 between the first both-sides planar portions 21 each of which is provided to the corresponding first hinge portion 15 is equal to a distance a2 (a distance between the second both-sides planar portions 41) between the second hinge portions 30. A second wire receiver 36 is provided in one of the pair of second circumferential wall portions 31. The second wire receiver 36 is formed by the same manufacturing method as that of the first wire receiver 28. The second wire receiver 36 is arranged to be apart from each second hinge portion 30 at 90° in the circumferential direction of the second nodal ring 13. Here, the circumferential length S2 is a length which does not include a protruding portion of the second wire receiver 36.

It is to be noted that the second nodal ring 13 is formed by bringing both end surfaces of a second nodal ring preliminary body 13a into contact with each other and joining and connecting a part or entire of the contacted portions as will be described later. As a result, a second joint portion 38 is formed in the second nodal ring 13 along the axial direction (the longitudinal direction) of the second nodal ring 13.

FIG. 6 is a cross-sectional view taken along a line VI-VI in FIG. 3. As shown in FIG. 3 and FIG. 6, when the through hole 26 in each first tongue piece portion 25 engages with the protruding portion 35 on the corresponding second tongue piece portion 33, the first nodal ring 12 and the second nodal ring 13 are coupled with each other to allow each of them to rotate. At this time, since the distance a1 between the first both-sides planar portions 21 each of which is provided to the corresponding first hinge portions 15 is equal to the distance a2 between the second hinge portions 30, the first both-sides planar portion 21 of each first hinge portion 15 and each second hinge portion 30 are arranged on the same plane as shown in FIG. 6. The first central planar portion 20 arranged to the outer side than the first both-sides planar portion 21 by a distance corresponding to the wall thickness of the first nodal ring 12 is arranged to the outer peripheral side of the bending tube 10 than the second hinge portion 30 (the second central planar portion 40) by a distance corresponding to the wall thickness of each of the first nodal ring 12 and the second nodal ring 13. Therefore, the first nodal ring 12 and the second nodal ring 13 are coupled with each other in a state that the inner peripheral surface of each first central planar portion 20 is in contact with the outer peripheral surface of each second hinge portion 30 (each second central planar portion 40) without gap. Furthermore, to prevent disengagement of the through hole 26 and the protruding portion 35, a retaining portion 39, a diameter d1 of which is expanded beyond a diameter d2 of the through hole 26, is formed to the protruding portion 35.

When the first nodal ring 12 is coupled with the second nodal ring 13, the first wire receiver 28 and the second wire receiver 36 are arranged to be apart from each other at 180° in the circumferential direction of the bending tube 10. The bending tube 10 is operated to bend in two directions by each operation wires inserted into the first wire receiver 28 or the second wire receiver 36. It is to be noted that the bending tube 10 is configured to bend in the two directions in this embodiment, but it may be configured to bend in four directions.

Further, when the first nodal ring 12 is coupled with the second nodal ring 13, an angle from the first hinge portion 15 to the first joint portion 29 is substantially equal to an angle from the second hinge portion 30 to the second joint portion 38 in the circumferential direction of the bending tube 10. The both-end nodal ring 11 will now be described.

FIG. 7 is a cross-sectional view taken along a line VII-VII in FIG. 2. As shown in FIG. 2 and FIG. 7, the both-end nodal ring 11 includes a pair of both-end nodal ring hinge portions 47 symmetrically provided about the central axis with respect to each other, and a pair of both-end nodal ring peripheral wall portions 48 each of which is provided between the both-end nodal ring hinge portions 47. A both-end nodal ring ridge line 96 is formed between the both-end nodal ring hinge portion 47 and the both-end nodal ring peripheral wall portion 48. The both-end nodal ring hinge portion 47 includes a both-end nodal ring central planar portion 90, both-end nodal ring both-sides planar portion 91 provided on both sides of the both-end nodal ring central planar portion 90 in the circumferential direction of the both-end nodal ring 11 (the bending tube 10), and axial step portions 93 formed between the both-end nodal ring central planar portion 90 and the both-end nodal ring both-sides planar portion 91. That is, the both-end nodal ring hinge portion 47 has substantially the same configuration as that of the first hinge portion 15 of the first nodal ring 12.

However, as shown in FIG. 2, in the both-end nodal ring hinge portion 47 of the both-end nodal ring 11, a both-end nodal ring tongue piece portion 95, which is a both-end nodal ring coupling portion, is provided at one end portion alone of the both-end nodal ring central planar portion 90 in the axial direction (the longitudinal direction) of the both-end nodal ring 11. In this embodiment, the both-end nodal ring tongue piece portion 95 has the same configuration as that of the first tongue piece portion 25, and a through hole 26 is formed in a central part of the both-end nodal ring tongue piece portion 95. When the through hole 26 in the both-end nodal ring tongue piece portion 95 engages with the protruding portion 35 on the corresponding second tongue piece portion 33, the both-end nodal ring 11 is coupled with the second nodal ring 13. At the end portion of the both-end nodal ring hinge portion 47 on the opposite side of the side where the both-end nodal ring tongue piece portion 95 is arranged, a fitting portion 49 is provided to protrude toward the opposite direction of the direction where the both-end nodal ring tongue piece portion 95 is arranged. The front-end nodal ring 11A is fitted to the distal-end hard portion 6 through the fitting portion 49, and the rear-end nodal ring 11B is fitted to the flexible tube 4 through the fitting portion 49.

The both-end nodal ring circumferential wall portion 48 has substantially the same configuration as the first circumferential wall portion 16 of the first nodal ring 12, and it is formed into a circumferential surface shape. However, the first wire receiver 28 is not provided in the both-end nodal ring circumferential wall portion 48. Furthermore, like the first nodal ring 12, a both-end nodal ring joint portion 97 is formed in the both-end nodal ring 11.

Figure 8:
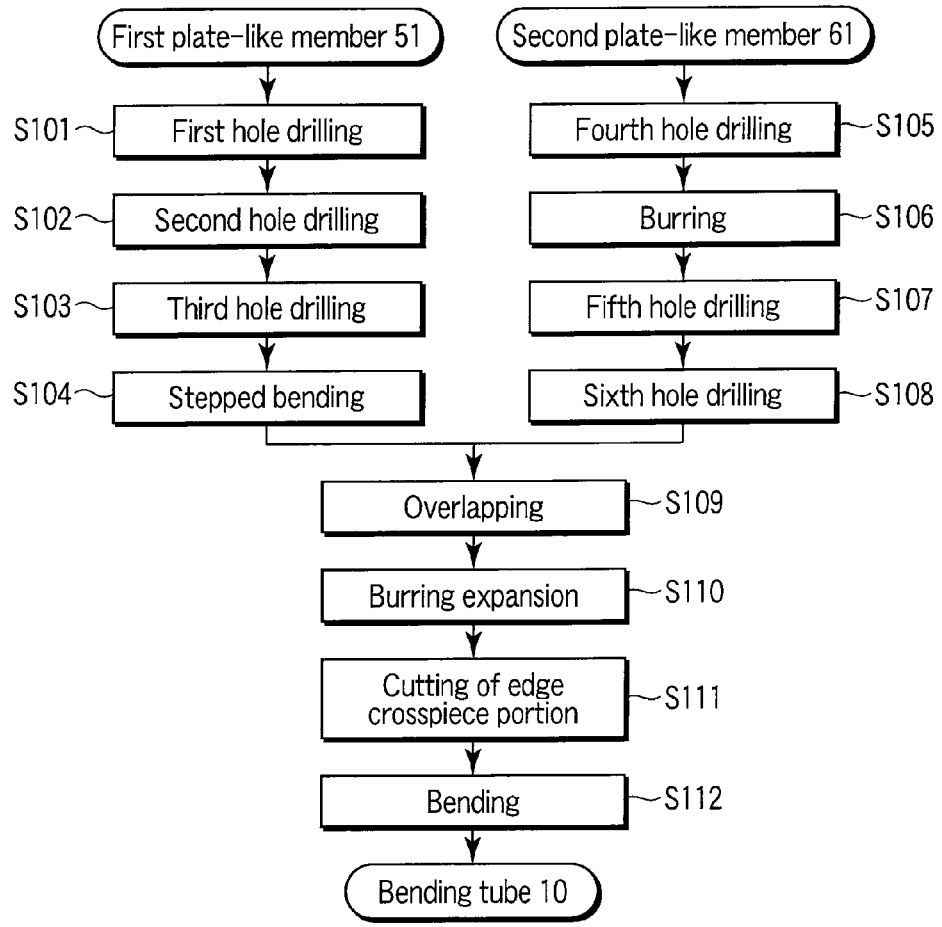
FIG. 8 is a flowchart showing a manufacturing process of a bending tube according to the first embodiment.

A manufacturing method of the bending tube 10 according to this embodiment will now be described. FIG. 8 is a flowchart showing manufacturing process of the bending tube 10.

As shown in FIG. 8, first, at steps S101 to S104, a metal first plate-like member 51 is processed to form both-end nodal ring preliminary bodies 11a constituting the both-end nodal rings 11 and first nodal ring preliminary bodies 12a constituting the first nodal rings 12. The steps S101 to 104 will now be described hereinafter. It is to be noted that the steps S101 to S104 are carried out based on press work using a die.

Figure 9:
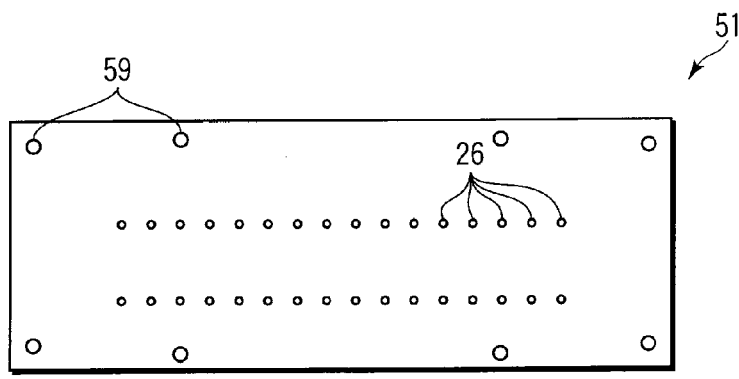
FIG. 9 is a plan view showing a first plate-like member according to the first embodiment in a state after performing a first hole drilling.

FIG. 9 is a view showing the first plate-like member 51 in a state that after performing the first hole drilling S101. As shown in FIG. 9, the through holes 26 are formed in the both-end nodal ring tongue portions 95 of each both-end nodal ring 11 and in the first tongue portions 25 of each first nodal ring 12.

Figure 10A:
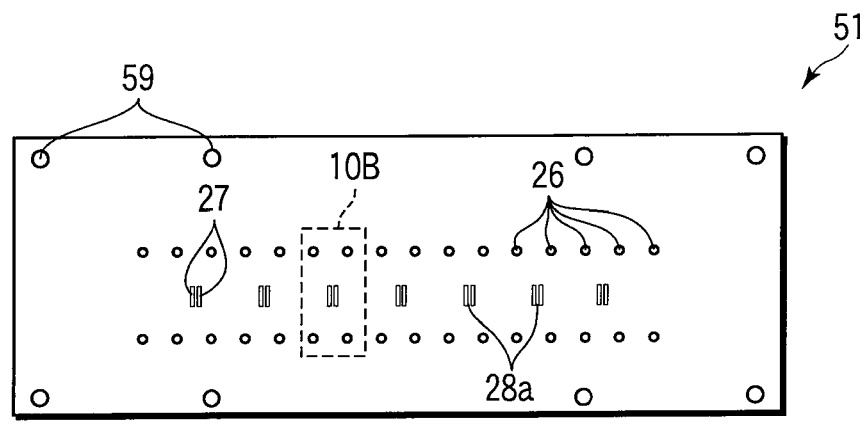
FIG. 10A is a plan view showing the first plate-like member according to the first embodiment in a state after performing a second hole drilling.
Figure 10B:
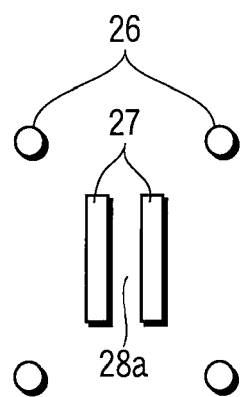
FIG. 10B is an enlarged plan view showing a range 10B in FIG. 10A.

FIG. 10A is a view showing the first plate-like member 51 in a state that after performing the second hole drilling S102. As shown in FIG. 10A, based on the second hole drilling S102, first wire receiver preliminary portions 28a constituting the first wire receivers 28 in the first nodal rings 12 are formed. FIG. 10B is an enlarged view showing a range 10B in FIG. 10A. As shown in FIG. 10B, the first wire receiver preliminary portion 28a includes two slits 27. After carrying out a later-described bending S112 to form the first nodal ring preliminary bodies 12 into circular shapes, the first wire receiver 28 is formed by inwardly protruding a strip-like portion between the two slits 27 in a C-like shape in the radial direction of the first nodal ring 12.

Figure 11:
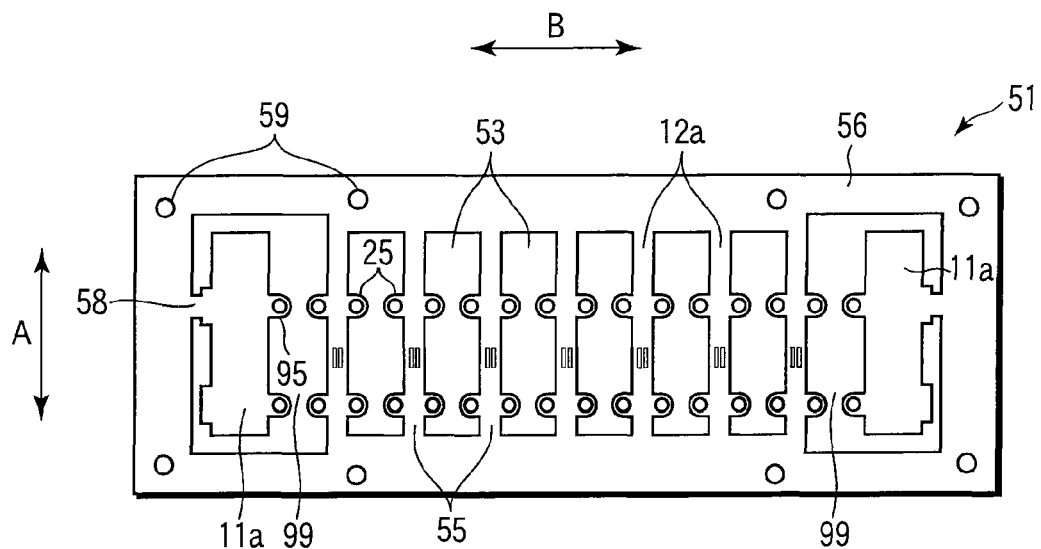
FIG. 11 is a plan view showing the first plate-like member according to the first embodiment in a state after performing a third hole drilling.

FIG. 11 is a view showing the first plate-like member 51 in a state that after carrying out the third hole drilling S103. As shown in FIG. 11, based on the third hole drilling S103, the both-end nodal ring preliminary bodies 11a constituting the both-end nodal rings 11 and the first nodal ring preliminary bodies 12a constituting the first nodal rings 12 are formed. A gap 53, which is appropriate for arrangement of each second nodal ring preliminary bodies 13a constituting the second nodal ring 13, is formed between the respective first nodal ring preliminary bodies 12a. Likewise, a gap 99, which is appropriate for arrangement of each second nodal ring preliminary bodies 13a, is formed between the both-end nodal ring preliminary body 11a and the first nodal ring preliminary body 12a. The both-end nodal ring tongue piece portions 95 are formed to each both-end nodal ring preliminary body 11a, and the first tongue piece portions 25 are formed to each first nodal ring preliminary body 12a. At this time, both end portions of each strip-like first nodal ring preliminary body 12 are coupled with a first edge 56 at first edge crosspiece portions 55 in the circumferential direction (a direction indicated by an arrow A in FIG. 11) of the bending tube 10. Moreover, an end portion of each both-end nodal ring preliminary body 11a on the opposite side of the side where the both-end nodal ring tongue piece portions 95 are provided is coupled with the first edge 56 of the first plate-like member 51 at a both-end edge crosspiece portion 58 in the axial direction (a direction indicated by an arrow B in FIG. 11) of the bending tube 10. Eight first positioning holes 59 are provided in the first edge 56 of the first plate-like member 51. It is to be noted that one end portion alone of each first nodal ring preliminary body 12a may be coupled with the first edge 56 of the first plate-like member 51 at the first edge crosspiece portion 55, and the other end portion of the same may not be coupled with the first edge 56.

Figure 12:
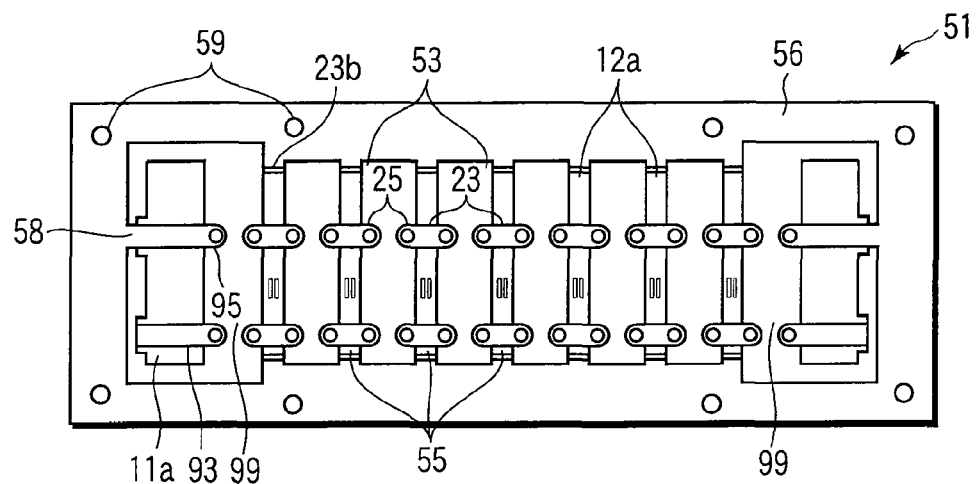
FIG. 12 is a plan view showing the first plate-like member according to the first embodiment in a state after performing a stepped bending.
Figure 13A:
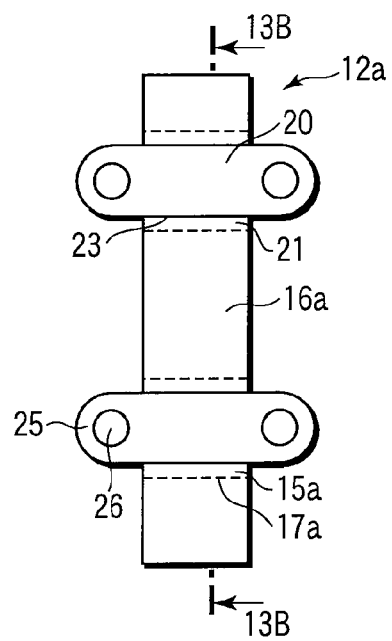
FIG. 13A is a plan view showing a first nodal ring preliminary body according to the first embodiment in a state after performing a stepped bending.
Figure 13B:
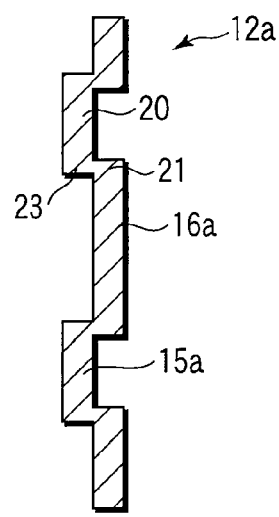
FIG. 13B is a cross-sectional view taken along a line 13B-13B in FIG. 13A.

FIG. 12 is a view showing the first plate-like member 51 in a state that after performing the stepped bending S104. As shown in FIG. 12, based on the stepped bending S104, the axial step portions 93 are formed on the both-end nodal ring preliminary bodies 11a, and the axial step portions 23 are formed on the first nodal ring preliminary bodies 12a. FIG. 13A is a view showing the first nodal ring preliminary body 12a in the state that after performing the stepped bending S104, and FIG. 13B is a cross-sectional view taken along a line 13B-13B in FIG. 13A. As shown in FIG. 13A and FIG. 13B, each first nodal ring preliminary body 12a after carrying out the stepped bending includes first hinge portion preliminary portions 15a and first circumferential wall portion preliminary portions 16a. A first ridge line forming portion 17a constituting the first ridge line 17, after carrying out a later-described bending S112 to form each first nodal preliminary body 12a into a circular shape, is formed between the first hinge portion preliminary portion 15a and the first circumferential portion preliminary portion 16a. The step is formed between the first central planar portion 20 and the first both-sides planar portion 21 of each the first hinge portion preliminary portion 15a of the first nodal ring preliminary body 12a by each axial step portion 23. A step between the first central planar portion 20 and the first both-sides planar portion 21 at the axial step portion 23 is equal to a wall thickness of the first nodal ring preliminary body 12a. At this time, a step portion 23b is formed between the edge 56 of the first plate-like member 51 and each first nodal ring preliminary body 12a by stepped bending processing. Providing the step portion 23b enables the edge 56 of the first plate-like member 51 and the first central planar portion 20 to be arranged on the same plane.

Likewise, the both-end nodal ring central planar portion 90 and the both-end nodal ring both-sides planar portion 91 are formed in each both-end nodal ring hinge portion preliminary portion 47a of the both-end nodal ring preliminary body 11a by each axial step portion 93.

Then, at steps S105 to S108, a metal second plate-like member 61 is processed to form second nodal ring preliminary bodies 13a constituting the second nodal rings 13. The steps S105 to 108 will now be described hereinafter. It is to be noted that the steps S105 to 108 are carried out based on press work using a die.

Figure 14A:
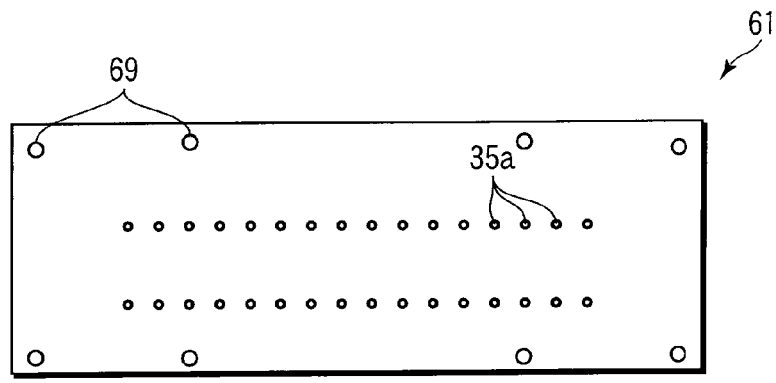
FIG. 14A is a plan view showing a second plate-like member according to the first embodiment in a state after performing a fourth hole drilling.
Figure 14B:
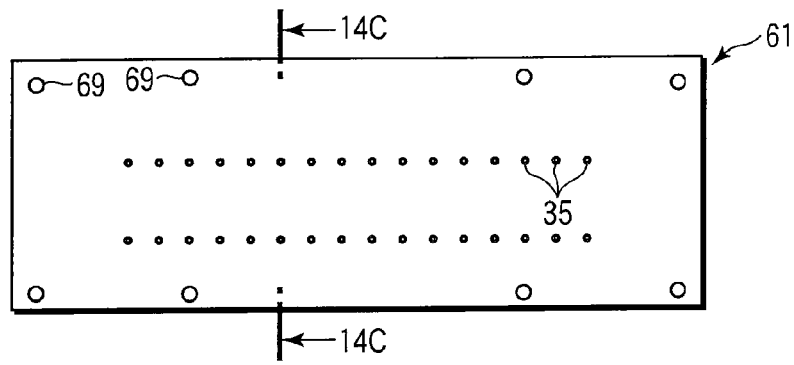
FIG. 14B is a plan view showing the second plate-like member according to the first embodiment in a state after performing a burring.
Figure 14C:
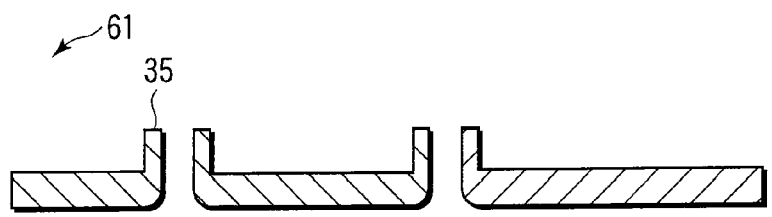
FIG. 14C is a cross-sectional view taken along a line 14C-14C in FIG. 14B.

FIG. 14A is a view showing the second plate-like member 61 in a state that after performing the fourth hole drilling S105, and FIG. 14B and FIG. 14C are views showing a state after carrying out the burring S106. As shown in FIG. 14A, prepared holes 35a of burring are formed by the fourth hole drilling S105. As shown in FIG. 14B and FIG. 14C, the protruding portions 35 are formed in the second tongue piece portions 33 of each second nodal ring 13 by the burring S106.

FIG. 15 is a view showing the second plate-like member 61 in a state that after effecting the fifth hole drilling S107. As shown in FIG. 15, second wire receiver preliminary portions 36a constituting the second wire receivers 36 of the second nodal rings 13 are formed by the fifth hole drilling S107. The second wire receiver preliminary portion 36a includes two slits 27 like the first wire receiver preliminary portion 28a, and the second wire receiver 36 is formed by the same manufacturing method as that of the first wire receiver 28.

FIG. 16 is a view showing the second plate-like member 61 in a state that after performing the sixth hole drilling S108. As shown in FIG. 16, the second nodal ring preliminary bodies 13a constituting the second nodal rings 13 are formed by the sixth hole drilling S108. A gap 65, which is appropriate for arrangement of each first nodal ring preliminary body 12a, is formed between the respective second nodal ring preliminary bodies 13a. Likewise, a gap 67, which is appropriate for arrangement of each both-end nodal ring preliminary body 11a, is formed between the second edge 62 of the second plate-like member 61 and the second nodal ring preliminary body 13a. The second tongue piece portions 33 are formed to each second nodal ring preliminary body 13a. At this time, both end portions of each strip-like nodal ring preliminary body 13a are coupled with the second edge 62 at second edge crosspiece portions 68 in the circumferential direction (a direction indicated by an arrow C in FIG. 16) of the bending tube 10. Eight first positioning holes 69 are formed in the second edge 62 of the second plate-like member 61. It is to be noted that one end portion alone of each second nodal ring preliminary body 13a may be coupled with the second edge 62 of the second plate-like member 61 at the second edge crosspiece portion 68, and the other end portion of the same may not be coupled with the second edge 62.

FIG. 17 is a view showing the second nodal ring preliminary body 13a in a state after performing the sixth hole drilling S108. As shown in FIG. 17, the second nodal ring preliminary body 13a includes second hinge portion preliminary portions 30a and second circumferential wall preliminary portions 31a. Second ridge line forming portion 32a, which is configured to form the second ridge lines 32 after effecting a later-described bending S112 to form each first nodal ring preliminary body 12a into a circular shape, are provided between the second hinge portion preliminary portion 30a and the second circumferential wall portion preliminary portion 31a. Each second hinge portion preliminary portion 30a includes the second central planar portion 40 and the second both-sides planar portion 41. The second central planar portion 40 and the second both-sides planar portion 41 are arranged on the same plane.

Additionally, an overlapping S109 and a burring expanding S110 are carried out to couple the first nodal ring preliminary bodies 12a with the second nodal ring preliminary bodies 13a. Likewise, the both-end nodal ring preliminary bodies 11a are coupled with the second nodal ring preliminary bodies 13a.

FIG. 18A is a view showing a state after performing the overlapping S109 and the burring expanding S110. As shown in FIG. 18A, at the overlapping S109, the second plate-like member 61 is arranged in a state that the protruding portions 35 of the second tongue piece portions 33 protrude toward the upper side. Further, the first plate-like member 51 is overlapped from the upper side of the second plate-like member 61 in a state that the first central planar portions 20 are arranged to be higher than the first both-sides planar portions 21. At this time, the first plate-like member 51 and the second plate-like member 61 are overlapped on each other by utilizing, e.g., positioning mechanisms and the like in the die at positions where the first positioning holes 59 of the first plate-like member 51 and the second positioning holes 69 of the second plate-like member 61 overlap each other. When the overlapping process is effected at the positions where each first positioning hole 59 of the first plate-like member 51 and the corresponding second positioning hole 69 of the second plate-like member 61 overlap, the both-end nodal ring preliminary bodies 11a, the first nodal ring preliminary bodies 12a, and the second nodal ring preliminary bodies 13a are arranged at appropriate positions. Furthermore, the protruding portion 35 of each second tongue piece portion 33 is inserted into the through hole 26 of the corresponding first tongue piece portion 25 to engage the through hole 26 and the protruding portion 35 with each other, whereby the first nodal ring preliminary bodies 12a and the second nodal ring preliminary bodies 13a are coupled with each other. Likewise, when the protruding portion of each second tongue piece portion 33 engage with the through hole 26 of the corresponding both-end nodal ring tongue piece portion 95, the both-end nodal ring preliminary bodies 11a and the second nodal ring preliminary bodies 13a are coupled with each other.

FIG. 18B is a view showing a state at the time of the burring expanding S110. As shown in FIG. 18B, the burring expanding S110 is carried out by using an expanding punch 37. Based on the burring expanding S110, a retaining portion 39 is formed at a protruding end of the protruding portion 35. A diameter d1 of the retaining portion 39 is expanded to be larger than a diameter d2 of the through hole 26.

Further, the edge crosspiece portion cutting S111 is carried out. FIG. 19 is a view showing a state after effecting the edge crosspiece portion cutting S111. As shown in FIG. 19, at the edge crosspiece portion cutting S111, the first edge crosspiece portions 55 of the first plate-like member 51 are cut, whereby the first nodal ring preliminary bodies 12a are cut off from the first edge 56 of the first plate-like member 51. Further, the second edge crosspiece portions 68 of the second plate-like member 61 are cut, whereby the second nodal ring preliminary bodies 13a are cut off from the second edge 62 of the second plate-like member 61. The both-end nodal ring preliminary bodies 11a are kept in the state coupled with first edge 56 of the first plate-like member 51 at the both-end edge crosspiece portions 58. It is to be noted that the edge crosspiece portion cutting S111 is carried out based on press work using a die.

Furthermore, the bending S112 is performed, and then the both-end nodal ring preliminary bodies 11a are disconnected from the first edge 56 of the first plate-like member 51 by cutting the both-end edge crosspiece portions 58 of the first plate-like member 51, thereby forming the bending tube 10. The bending S112 is carried out by bending the first circumferential wall portion preliminary portions 16a of each nodal ring preliminary body 12a into a U-like shape by press work using a die and then bending the same into an O-like shape. The same bending is effected with respect to the second circumferential wall portions 31a of each second nodal ring preliminary body 13 and the both-end nodal ring circumferential wall portion preliminary portions 48a of each both-end nodal ring preliminary body 11a.

FIG. 20 is a view showing a state after performing the bending S112. As shown in FIG. 20, the first nodal rings 12 are formed from the first nodal ring preliminary bodies 12a, the second nodal rings 13 are formed from the second nodal ring preliminary bodies 13a, and the both-end nodal rings 11 are formed from the both-end nodal ring preliminary bodies 11a by effecting the bending S112. At this time, a first abutting portion 29a at which both end surfaces abut on each other is formed in each first nodal ring preliminary body 12a. Likewise, a both-end nodal ring abutting portion 97a at which both end surfaces abut on each other is formed in each both-end nodal ring preliminary body 11a. When a part or entire of the first abutting portion 29a is joined and connected by, e.g., laser welding, the first joint portion 29 is formed along the axial direction (the longitudinal direction) of the first nodal ring 12. Likewise, when a part or entire of the both-end nodal ring abutting portion 97a is joined and connected by, e.g., laser welding, the both-end nodal ring joint portion 97 is formed along the longitudinal direction. A second abutting portion 38a at which both end surfaces abut on each other is formed in each second nodal ring preliminary body 13a. When a part or entire of the second abutting portion 38a is joined and connected, the second joint portion 38 is formed along the axial direction (the longitudinal direction) of the second nodal ring 13.

A function of the bending portion 5 of the endoscope 1 according to this embodiment will now be described.

In the bending tube 10 of the bending portion 5, the first nodal ring preliminary bodies 12a are formed in the first plate-like member 51, the second nodal ring preliminary bodies 13a are formed in the second plate-like member 61, and the first plate-like member 51 and the second plate-like member 61 are overlapped on each other, whereby the first nodal ring preliminary bodies 12a are coupled with the second nodal ring preliminary bodies 13a. At this time, the through hole 26 in each first tongue piece portion 25 of each first nodal ring preliminary body 12a engages with the protruding portion 35 on the corresponding second tongue piece portion 33 of the corresponding second nodal ring preliminary body 13a. Likewise, the both-end nodal ring preliminary bodies 11a are formed in the first plate-like member 51, and the through hole 26 of each both-end nodal ring tongue piece portion 95 of each both-end nodal ring preliminary body 11a engages with the protruding portion 35 on the corresponding second tongue piece portion 33 of the corresponding second nodal ring preliminary body 13a. Further, the first nodal rings 12 and the second nodal rings 13 are formed by bending the first circumferential wall portion preliminary portions 16a of each first nodal ring preliminary body 12a and the second circumferential wall portion preliminary portions 31a of each second nodal ring preliminary body 13a. Likewise, the both-end nodal rings 11 are formed by bending the both-end nodal ring circumferential wall portion preliminary portions 48a of each both-end nodal ring preliminary body 11a. As described above, the bending tube 10 is formed without forming the both-end nodal rings 11 separately from the other nodal rings 12 and 13. Moreover, coupling strength and rotational movement characteristics between the first nodal rings 12 and the second nodal rings 13 can be assured by coupling the first nodal ring preliminary bodies 12a and the second nodal ring preliminary bodies 13a before the bending process. Likewise, coupling strength and rotational movement characteristics between the both-end nodal rings 11 and the second nodal rings 13 can be assured.

Additionally, in the bending tube 10 of the bending portion 5, the distance a1 between the first both-sides planar portions 21 each of which is provided to the corresponding first hinge portions 15 is equal to the distance a2 between second hinge portions 30 (second both-sides planar portions 41). Therefore, each first both-sides planar portion 21 of the first hinge portion 15 and each second hinge portion 30 are arranged on the same plane. At this time, the first central planar portion 20, which is arranged to the outer side than the first both-sides planar portion 21 by a distance corresponding to the wall thickness of the first nodal ring 12, is arranged to the outer peripheral side of the bending tube 10 than the second hinge portion 30 (the second central planar portion 40) by a distance corresponding to the wall thickness of each of the first nodal ring 12 and the second nodal ring 13. Therefore, in a state that the planar inner peripheral surface of each first central planar portion 10 is in contact with the planar outer peripheral surface of the corresponding second hinge portion 30 (the corresponding second central planar portion 40) with no space between them, the first nodal ring 12 is coupled with the second nodal ring 13. When these nodal rings are coupled with each other in the state that the planar inner peripheral surface is in contact with the planar outer peripheral surface with no space between them, coupling strength and rotational movement characteristics between the first nodal rings and the second nodal ring preliminary bodies 13a can be assured. Likewise, coupling strength and rotational movement characteristics between the both-end nodal rings 11 and the second nodal rings 13 can be also assured.

Further, in the bending tube 10 of the bending portion 5, the first circumferential dimension S1 which is the sum of the length L1 of the pair of the first hinge portions 15 in the circumferential direction of the first nodal ring 12 and the circumferential length L2 of the pair of the first circumferential wall portions 16 is equal to the second circumferential dimension S2 which is the sum of the length L3 of the pair of the second hinge portions 30 in the circumferential direction of the second nodal ring 13 and the circumferential length L4 of the pair of the second circumferential portions 31. Further, cross-sectional shapes of the first circumferential portion 16 and the second circumferential portion 31 perpendicular to the axial direction of the bending tube 10 (which are a first cross-sectional shape and a second cross-sectional shape, respectively) are congruent with each other. Adopting such a configuration enables forming the first nodal rings 12 and the second nodal rings 13 that the distance a1 between the first both-sides planar portions 21 each of which is provided to the corresponding first hinge portion 15 is equal to the distance a2 between the second hinge portions 30 (the second both-sides planar portions 41). Likewise, both-end nodal rings 11 that a distance between the both-end nodal ring both-sides planar portions 91 each of which provided to the corresponding both-end nodal ring hinge portion 47 is equal to the distance a1 and the distance a2 are formed.

Furthermore, in the bending tube 10 of the bending portion 5, after engaging the through hole 26 in each first tongue piece portion 25 of each first nodal ring preliminary body 12a with the protruding portion 35 in the corresponding second tongue piece portion 33 of the corresponding second nodal ring preliminary body 13a, the retaining portions 39 are formed at the protruding ends of the protruding portions 35 by the burring expansion. Forming the retaining portions 35 enables coupling strength and rotational movement characteristics to be assured between the first nodal rings and the second nodal ring preliminary bodies 13a. Likewise, coupling strength and the rotational movement characteristics can be assured between the both-end nodal rings 11 and the second nodal rings 13.

Therefore, the bending portion 5 of the endoscope 1 having the above-described configuration exhibits the following effects. That is, in the bending tube 10 of the bending portion 5 according to this embodiment, the first circumferential dimension S1 which is the sum of the length L1 of the pair of the first hinge portions 15 in the circumferential direction of the first nodal ring 12 and the circumferential length L2 of the pair of the first circumferential wall portions 16 is equal to the second circumferential dimension S2 which is the sum of the length L3 of the pair of the second hinge portions 30 in the circumferential direction of the second nodal ring 13 and the circumferential length L4 of the pair of the second circumferential wall portions 31. Furthermore, the cross-sectional shapes of the first circumferential wall portion 16 and the second circumferential wall portion 31 perpendicular to the axial direction of the bending tube 10 (which are the first cross-sectional shape and the second cross-sectional shape, respectively) are congruent with each other. When such a configuration is adopted, it is possible to provide the first nodal rings 12 and the second nodal rings 13 that the distance a1 between the first both-sides planar portions 21 each of which is provided to the corresponding first hinge portion 15 is equal to the distance a2 between the second hinge portions 30 (the second both-sides planar portions 41). Likewise, it is possible to provide the both-end nodal rings 11 that the distance between the both-end nodal ring both-sides planar portions 91 each of which is provided to the corresponding both-end nodal ring hinge portion 47 is equal to the distance a1 and the distance a2. Therefore, the bending tube 10 is formed without forming the both-end nodal rings 11 separately from the other nodal rings 12 and 13. As a result, workability of forming and assembling the bending tube 10 can be improved, and a manufacturing cost can be suppressed.

Moreover, each strip-like first nodal ring preliminary body 12a is coupled with the corresponding strip-like second nodal ring preliminary body 13a, and then the bending S112 is carried out. When the first nodal ring preliminary body 12a is coupled with the second nodal ring preliminary body 13a in the tabular state, coupling strength and rotational movement characteristics between the first nodal ring 12 and the second nodal ring 13 can be assured. Likewise, coupling strength and rotational movement characteristics of the both-end nodal ring 11 and the second nodal ring 13 can also be assured.

Additionally, in the bending tube 10 of the bending portion 5, the distance a1 between the first both-sides planar portions 21 each of which is provided to the corresponding first hinge portion 15 is equal to the distance a2 between the second hinge portions 30 (the second both-side planar portions 41). Therefore, the first both-sides planar portion 21 of each first hinge portion 15 and each second hinge portion 30 are arranged on the same plane. At this time, the first central planar portion 20, which is arranged to the outer side than the first both-sides planar portion 21 by a distance corresponding to the wall thickness of the first nodal ring 12, is arranged to the outer peripheral side of the bending tube 10 than the second hinge portion 30 (the second central planar portion 40) by a distance corresponding to the wall thickness of each of the first nodal ring 12 and the second nodal ring 13. Therefore, in the state that the planar inner peripheral surface of each first central planar portion 20 is in contact with the planar outer peripheral surface of each second hinge portion 30 (each second central planar portion 40) with no space therebetween, the first nodal ring 12 is coupled with the second nodal ring 13. When the planar inner peripheral surface is coupled with the planar outer peripheral surface with no space therebetween, coupling strength and rotational movement characteristics between the first nodal ring 12 and the second nodal ring 13 can be assured. Likewise, coupling strength and rotational movement characteristics between the both-end nodal ring 11 and the second nodal ring 13 can be also assured.

Additionally, in the bending tube 10 of the bending portion 5, the through hole 26 in each first tongue piece portion 25 of each first nodal ring preliminary body 12 is engaged with the protruding portion 35 on the corresponding second tongue piece portion 33 of the corresponding second nodal ring preliminary body 13a, and the retaining portions 39 are formed at protruding ends of the protruding portions 35 by the burring expansion. Forming the retaining portions 39 enables assuring coupling strength and rotational movement characteristics between the first nodal rings and the second nodal ring preliminary bodies 13a. Likewise, coupling strength and rotational movement characteristics between the both-end nodal rings 11 and the second nodal rings 13 can also be assured.

First to fifth modifications of the first embodiment according to the present invention will now be described with reference to FIG. 21A to FIG. 25B. In the first to fifth modification, the configuration of the first embodiment is modified as follows. It is to be noted that like reference numerals denote parts equal to those in the first embodiment to omit a description thereof. Further, in the first to fifth modifications, the both-end nodal ring 11 has substantially the same configuration as that of the first nodal ring 12 except that the fitting portion 49 is provided at one end portion of this nodal ring 11 in the axial direction (the longitudinal direction) of the bending tube 10, thereby omitting a description thereof.

Figure 21A:
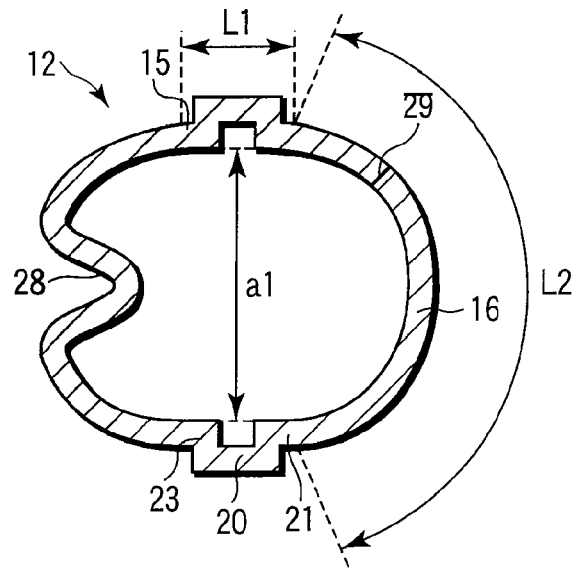
FIG. 21A is a cross-sectional view showing a first nodal ring according to a first modification of the first embodiment.
Figure 21B:
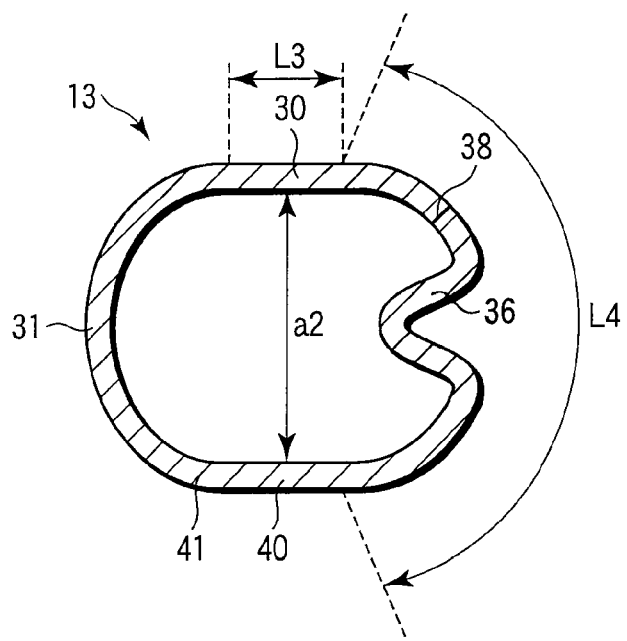
FIG. 21B is a cross-sectional view showing a second nodal ring according to the first modification of the first embodiment.

FIG. 21A is a view showing the first nodal ring 12 according to the first modification of the first embodiment, and FIG. 21B is a view showing the second nodal ring according to the second modification. As shown in FIG. 21A, in the first nodal ring 12 according to this modification, in a state that the distance a1 between the first both-sides planar portions 21 each of which is provided to the corresponding first hinge portion 15 in the first embodiment (see FIG. 4) is maintained, the length L1 of each first hinge portion 15 in the circumferential direction of the first nodal ring 12 is shortened, and the circumferential length L2 of each first circumferential wall portion 16 is extended. Likewise, as shown in FIG. 21B, in the second nodal ring 13, in a state that the distance a2 between the second hinge portions 30 (the second both-side planar portions 41) in the first embodiment (see FIG. 5) is maintained, the length L3 of each second hinge portion 30 in the circumferential direction of the second nodal ring 13 is shortened, and the circumferential length L4 of each second circumferential wall portion 31 is extended. The distance a2 between the second hinge portions 30 is equal to the distance a1 between the first central planar portions 21 each of which is provided to the corresponding first hinge portions 15.

FIG. 22A is a view showing the first nodal ring 12 according to the second modification of the first embodiment, and FIG. 22B is a view showing the second nodal ring according to the second modification. As shown in FIG. 22A, in the first nodal ring 12 according to this modification, in a state that the distance a1 between the first central planar portions 21 each of which is provided to the corresponding first hinge portions 15 in the first embodiment (see FIG. 4) is maintained, the length L1 of each first hinge portion 15 in the circumferential direction of the first nodal ring 12 is extended, and the circumferential length L2 of each first circumferential wall portion 16 is shortened. Likewise, as shown in FIG. 22B, in the second nodal ring 13, in a state that the distance a2 between the second hinge portions 30 (the second both-sides planar portions 41) in the first embodiment (see FIG. 5) is maintained, the length L3 of each second hinge portion 30 in the circumferential direction of the second nodal ring 13 is extended, and the circumferential length L4 of each second circumferential wall portion 31 is shortened. The distance a2 between the second hinge portions 30 is equal to the distance a1 between the first central planar portions 21 each of which is provided to the corresponding first hinge portions 15.

That is, according to the first and second modifications, it is sufficient for the first circumferential dimension S1, which is the sum of the length L1 of the pair of the first hinge portions 15 in the circumferential direction of the first nodal ring 12 and the circumferential length L2 of the pair of the first circumferential wall portions 16, to be equal to the second circumferential dimension S2, which is the sum of the length L3 of the pair of the second hinge portions 30 in the circumferential direction of the second nodal ring 13 and the circumferential length L4 of the pair of the second circumferential wall portions 31. That is, if the first circumferential dimension S1 is equal to the second circumferential dimension S2, the length L1 of each first hinge portion 15 in the circumferential direction of the first nodal ring 12 may be reduced as shown in FIG. 22A, and the length L3 of each second hinge portion 30 in the circumferential direction of the second nodal ring 13 may be increased as shown in FIG. 22B. In this case, the length L1 of each first hinge portion 15 in the circumferential direction of the first nodal ring 12 is not equal to the length L3 of each second hinge portion 30 in the circumferential direction of the second nodal ring 13, and the circumferential length L2 of each first circumferential wall portion 16 is not equal to the circumferential length L4 of each second circumferential wall portion 31, respectively. However, the distance a1 between the first both-sides planar portions 21 each of which is provided the corresponding first hinge portions 15 is equal to the distance a2 between the second hinge portions 30. Therefore, after performing the bending processing, the first central planar portion 20 of each first hinge portion 15 is arranged to the outer peripheral side of the bending tube 10 than each second hinge portion 30 (each second central planar portion 40) by a distance corresponding to the wall thickness of each of the first nodal ring 12 and the second nodal ring 13. As a result, in a state that the inner peripheral surface of each first central planar portion 20 is in contact with the outer peripheral surface of each second hinge portion 30 (each second central planar portion 40) with no space therebetween, the first nodal ring 12 is coupled with the second nodal ring 13. Likewise, if the first circumferential dimension S1 is equal to the second circumferential dimension S2, the length L1 of each first hinge portion 15 in the circumferential direction of the first nodal ring 12 may be increased as shown in FIG. 22A, and the length L3 of each second hinge portion 30 in the circumferential direction of the second nodal ring 13 may be reduced.

FIG. 23A is a view showing the first nodal ring 12 according to the third modification of the first embodiment, and FIG. 23B is a view showing the second nodal ring 13 according to the third modification. As shown in FIG. 23A, in the first nodal ring 12 according to this modification, the distance a1 between the first both-sides planar portions 21 each of which is provide to the corresponding first hinge portion 15 is reduced from the first embodiment (see FIG. 4). In this case, as shown in FIG. 23B, the distance a2 between the second hinge portions 30 (the second both-side planar portions 41) of each second nodal ring 13 is reduced to be equal to the distance a1 between the first both-sides planar portions 21.

Figure 24A:
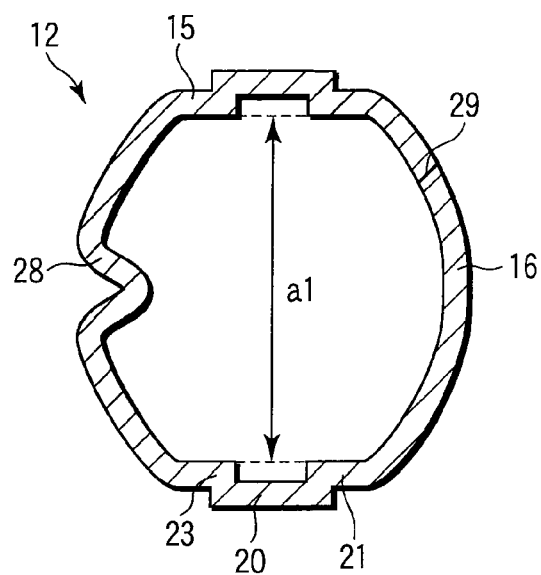
FIG. 24A is a cross-sectional view showing a first nodal ring according to a fourth modification of the first embodiment.
Figure 24B:
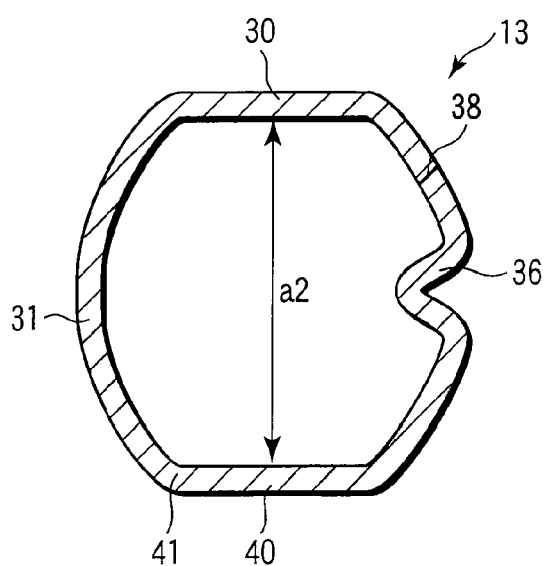
FIG. 24B is a cross-sectional view showing a second nodal ring according to the fourth modification of the first embodiment.

FIG. 24A is a view showing the first nodal ring 12 according to the fourth modification of the first embodiment, and FIG. 24B is a view showing the second nodal ring 13 according to the fourth modification. As shown in FIG. 24A, in the first nodal ring 12 according to this modification, the distance a1 between the first both-sides planar portions 21 each of which is provided to the corresponding first hinge portion 15 in the first embodiment (see FIG. 4) is increased. In this case, as shown in FIG. 24B, the distance a2 between the second hinge portions 30 (the second both-side planar portions 41) of each second nodal ring 13 is increased to be equal to the distance a1 between the first both-sides planar portions 21.

FIG. 25A is a view showing the first nodal ring 12 according to the fifth modification of the first embodiment, and FIG. 25B is a view showing the second nodal ring according to the fifth modification. The first circumferential wall portion 16 is formed into the cylindrical surface shape in the first nodal ring 12 according to the first embodiment (see FIG. 4), whereas the first circumferential wall portion 16 is constituted of a cylindrical surface portion 45, and a planar portions 46 each of which is provided between the first hinge portion 15 and the cylindrical surface portion 45 in the first nodal ring 12 according to this modification. Likewise, as shown in FIG. 25B, the second circumferential portion 31 is constituted of the cylindrical surface portion 45, and the planar portions 46 each of which is provided between the second hinge portion 30 and the cylindrical surface portion 45.

As described above, in the first to fifth modifications, the distance a1 between the first both-sides planar portions 21 each of which is provided to the corresponding first hinge portion 15 is equal to the distance a2 between the second hinge portions 30 (the second both-side planar portions 41). Based on such a configuration, the first central planar portion 20 of each first hinge portion 15 is arranged to the outer peripheral side of the bending tube 10 than the second hinge portion 30 (the second central planar portion 40) by a distance corresponding to the wall thickness of each of the first nodal ring 12 and the second nodal ring 13. Therefore, in the state that the planar inner peripheral surface of each first central planar portion 20 is in contact with the planar outer peripheral surface of each second central planar portion 40 with no space therebetween, the first nodal ring 12 is coupled with the second nodal ring 13. It is possible to change the length L1 of each first hinge portion 15 in the circumferential direction of the first nodal ring 12, the circumferential length L2 of each first circumferential wall portion 16, the cross-sectional shape of each first circumferential wall portion 16 (the first cross-sectional shape), the length L3 of each second hinge portion 30 in the circumferential direction of the second nodal ring 13, the circumferential length L4 of each second circumferential wall portion 31, and each cross-sectional shape of the second circumferential wall portion 31 (the second cross-sectional shape) within the scope of such a configuration. That is, it is sufficient for the first circumferential dimension S1 that is the sum of the length L1 of the pair of the first hinge portions 15 in the circumferential direction of the first nodal ring 12 and the circumferential length L2 of the pair of the first circumferential wall portions 16 to be equal to the second circumferential dimension S2 that is the sum of the length L3 of the pair of the second hinge portions 30 in the circumferential direction of the second nodal ring 13 and the circumferential length L4 of the pair of the second circumferential wall portions 31.

Sixth to ninth modifications of the first embodiment according to the present invention will now be described with reference to FIG. 26 to FIG. 33. In the sixth to ninth modifications, the configuration of the first embodiment is modified as follows. It is to be noted that like reference numerals denote parts equal to those in the first embodiment, thereby omitting a description thereof. Further, in the sixth to ninth modifications, since the both-end nodal ring 11 has substantially the same configuration as the first nodal ring 12 except that the fitting portion 49 is provided at one end portion in the axial direction of the bending tube 10, a description thereof will be omitted.

Figure 27A:
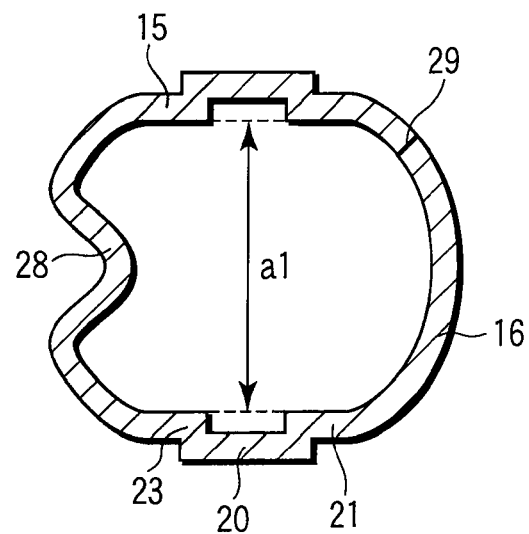
FIG. 27A is a cross-sectional view taken along a line 27A-27A in FIG. 26.
Figure 27B:
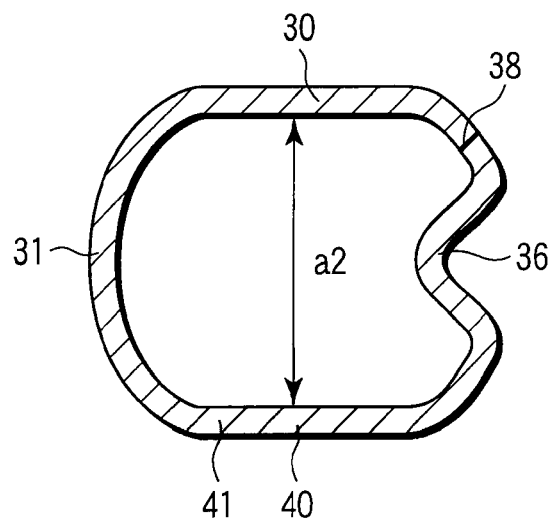
FIG. 27B is a cross-sectional view taken along a line 27B-27B in FIG. 26.

FIG. 26 is a view showing the first nodal ring 12 and the second nodal ring 13 of the sixth modification according to the first embodiment in a coupled state. FIG. 27A is a cross-sectional view taken along a line 27A-27A in FIG. 26, and FIG. 27B is a cross-sectional view taken along a line 27B-27B in FIG. 26. As shown in FIG. 26 and FIG. 27A, the first nodal ring 12 includes the pair of planar first hinge portions 15 symmetrically provided about the central axis (the axis in the longitudinal direction) with respect to each other, and the pair of first circumferential wall portions 16 each of which is provided between the first hinge portions 15 and has a cylindrical surface shape. Each first hinge portion 15 includes the first central planar portion 20, and the first both-sides planar portion 21 provided on both sides of the first central planar portion 20 in the circumferential direction of the first nodal ring 12 (the bending tube 10). The first both-sides planar portions 21 each of which is provided to the corresponding first hinge portion 15 are apart from each other by the distance a1. The axial step portions 23 are formed between the first central planar portion 20 and the first both-sides planar portion 21. When the axial step portion 23 is provided, the first central planar portion 20 is arranged to the outer peripheral side than the first both-sides planar portion 21 by a distance corresponding to the wall thickness of the first nodal ring 12. The first tongue piece portions 25 are provided at both end portions of each first central planar portion 20 in the axial direction (the longitudinal direction) of the first nodal ring 12. The protruding portion 35 protruding toward the inner peripheral side of the first nodal ring 12 is formed at the central part of each first tongue piece portion 25. The protruding portion 35 is formed by, e.g., burring processing.

As shown in FIG. 26 and FIG. 27B, the second nodal ring 13 includes the pair of second hinge portions 30 symmetrically provided about the central axis (the longitudinal axis) with respect to each other, and the pair of second circumferential wall portions 31 each of which is provided between the second hinge portions 30. Each of The second hinge portion 30 includes the second central planar portion 40 and the second both-sides planar portion 41 provided on both sides of the second central planar portion 40 in the circumferential direction of the second nodal ring 13 (the bending tube 10). In this modification, the second central planar portion 40 and the second both-sides planar portion 41 are formed on the same plane. Therefore, the second hinge portions 30 are formed into a planar shape, and the second hinge portions 30 are apart from each other by the distance a2 (the second both-side planar portions 41 are apart from each other by the distance a2). The distance a2 between the second hinge portions 30 is equal to the distance a1 between the first both-sides planar portions 21 each of which is provided the corresponding first hinge portion 15. The second tongue piece portions 33 are provided at both end portions of each second hinge portion 30 in the axial direction (the longitudinal direction) of the second nodal ring 13. The through hole 26 is formed at the central part of each second tongue piece portion 33.

When the protruding portion 35 of each first tongue piece portion 25 engages with the through hole 26 of the corresponding second tongue piece portion 33, the first nodal ring 12 and the second nodal ring 13 are coupled with each other to allow them to rotate. At this time, since the distance a1 between the first both-sides planar portions 21 each of which is provided the corresponding first hinge portion 15 is equal to the distance a2 between the second hinge portions 30, each first both-sides planar portion 21 and each second hinge portion 30 are arranged on the same plane. The first central planar portion 20, which is arranged to the outer side than the first both-sides planar portion 21 by a distance corresponding to the wall thickness of the first nodal ring 12, is arranged to the outer peripheral side of the bending tube 10 than the second hinge portion 30 (the second central planar portion 40) by a distance corresponding to the wall thickness of each of the first nodal ring 12 and the second nodal ring 13. Therefore, in the state that the inner peripheral surface of each first central planar portion 20 is in contact with the outer peripheral surface of each second central planar portion 40 with no space therebetween, the first nodal ring 12 is coupled with the second nodal ring 13. Further, the retaining portion 39 is formed on each protruding portion 39 to prevent the through hole 26 from being disengaged from the protruding portion 35.

Figure 28:
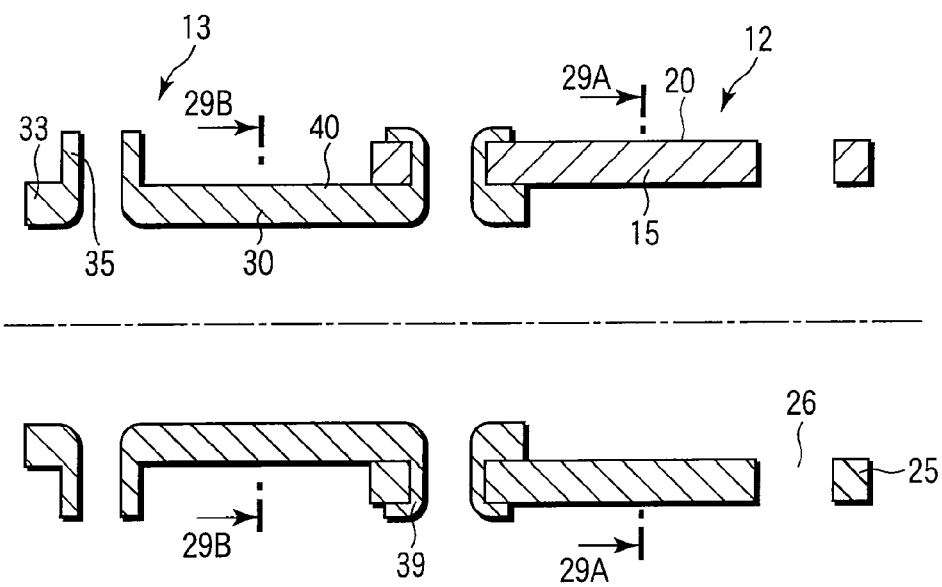
FIG. 28 is a cross-sectional view showing a first nodal ring and a second nodal ring according to a seventh modification of the first embodiment in a coupled state.

FIG. 28 is a view showing the first nodal ring 12 and the second nodal ring 13 of the seventh modification according to the first embodiment in a coupled state. FIG. 29A is a cross-sectional view taken along a line 29A-29A in FIG. 28, and FIG. 29B is a cross-sectional view taken along a line 29B-29B in FIG. 28. The first nodal ring 12 includes the pair of first hinge portions 15 symmetrically provided about the central axis (the longitudinal axis) with respect to each other, and the pair of first circumferential wall portions 16 each of which is provided between the second hinge portions 30 and has a cylindrical surface shape as shown in FIG. 28 and FIG. 29A. The first hinge portion 15 includes the first central planar portion 20, and the first both-sides planar portion 21 provided on both sides of the first central planar portion 20 in the circumferential direction of the first nodal ring 12 (the bending tube 10). In this modification, the first central planar portion 20 and the first both-sides planar portion 21 are formed on the same plane. Therefore, each first hinge portion 15 is formed into a planar shape, and the first hinge portions 15 are apart from each other by the distance a1 (the first both-side planar portions 21 are apart from each other by the distance a1). The first tongue piece portions 35 are provided at both end portions of each first hinge portion 15 in the axial direction (the longitudinal direction) of the first nodal ring 12. The through hole 26 is formed at the central part of each first tongue piece portion 25.

As shown in FIG. 28 and FIG. 29B, the second nodal ring 13 includes the pair of second hinge portions 30 symmetrically provided about the central axis (the axis in the longitudinal direction) with respect to each other, and the pair of second circumferential wall portions 31 each of which is provided between the second hinge portions 30. Each second hinge portion 30 includes the second central planar portion 40, and the second both-sides planar portion 41 provided on both sides of the second central planar portion 40 in the circumferential direction of the second nodal ring 13 (the bending tube 10). The second both-sides planar portions 41 each of which is provided to the corresponding second hinge portion 30 are apart from each other by the distance a2. The distance a2 is equal to the distance a1 between the first hinge portions 15 (the first both-side planar portions 21). The axial step portions 43 are formed between the second central planar portion 40 and the second both-sides planar portion 41. When the axial step portion 43 is provided, the second central planar portion 40 is arranged to the inner peripheral side of the second nodal ring 13 than the second both-sides planar portion 41 by a distance corresponding to the wall thickness of the second nodal ring 13. The second tongue piece portions 33 are provided at both end portions of each second both-sides planar portion 40 in the axial direction (the longitudinal direction) of the second nodal ring 13. The protruding portion 35 protruding toward the outer peripheral side of the second nodal ring 13 is formed at the central part of each second tongue piece portion 33. The protruding portion 35 is formed by, e.g., burring processing.

When the through hole 26 of each first tongue piece portion 25 engages with the protruding portion 35 of the corresponding second tongue piece portion 33, the first nodal ring 12 and the second nodal ring 13 are coupled with each other to allow each of them to rotate. At this time, since the distance a2 between the second both-sides planar portions 41 each of which is provided to the corresponding second hinge portion 30 is equal to the distance a1 between the first hinge portions 15, the second both-sides planar portion 41 of the second hinge portion 30 and the first hinge portion 15 (the first both-side planar portions 21) are arranged on the same plane. The second central planar portion 40, which is arranged to the inner side than the second both-sides planar portion 41 by a distance corresponding to the wall thickness of the second nodal ring 13, is arranged to the inner peripheral side of the bending tube 10 than the first hinge portion 15 (the first central planar portion 20) by a distance corresponding to the wall thickness of each of the first nodal ring 12 and the second nodal ring 13. Therefore, in the state that the inner peripheral surface of each first central planar portion 20 is in contact with the outer peripheral surface of each second central planar portion 40 with no space therebetween, the first nodal ring 12 is coupled with the second nodal ring 13. Further, the retaining portion 39 is formed on each protruding portion 35 to prevent the through hole 26 from being disengaged from the protruding portion 35.

Figure 30:
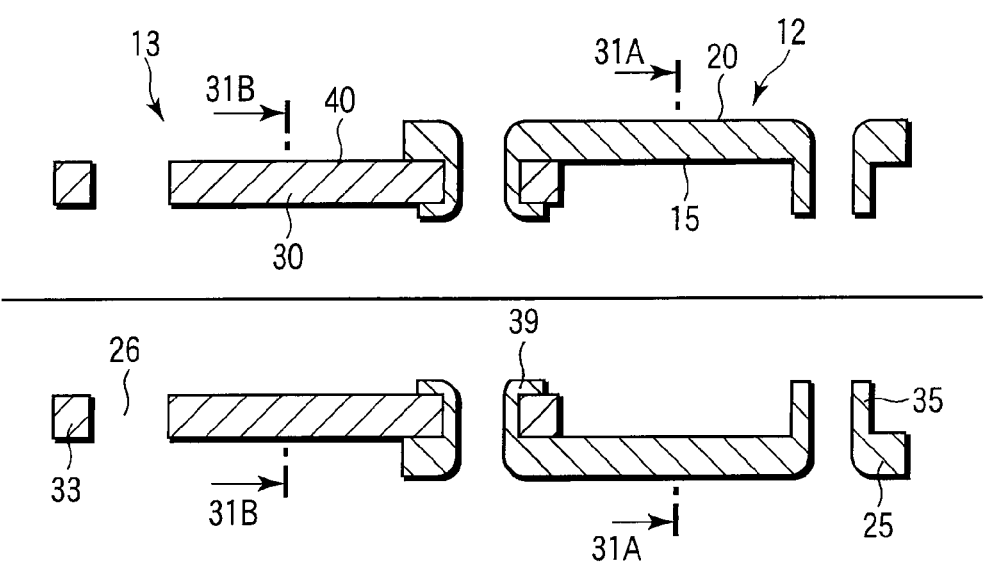
FIG. 30 is a cross-sectional view showing a first nodal ring and a second nodal ring according to an eighth modification of the first embodiment in a coupled state.

FIG. 30 is a view showing the first nodal ring 12 and the second nodal ring 13 of the eighth modification according to the first embodiment in a coupled state. FIG. 31A is a cross-sectional view taken along a line 31A-31A in FIG. 30, and FIG. 31B is a cross-sectional view taken along a line 31B-31B in FIG. 30. As shown in FIG. 30 and FIG. 31A, the first nodal ring 12 includes the pair of planar first hinge portions 15 symmetrically provided about the central axis (the axis in the longitudinal direction) with respect to each other, and the pair of first circumferential wall portions 16 each of which is provided between the first hinge portions 15 and has a cylindrical surface shape. Each first hinge portion 15 includes the first central planar portion 20, and the first both-sides planar portion 21 provided on both sides of the first central planar portion 20 in the circumferential direction of the first nodal ring 12 (the bending tube 10). In this modification, the first central planar portion 20 and the first both-sides planar portion 21 are formed on the same plane. Therefore, each first hinge portion 15 is formed into a planar shape, and the first hinge portions 15 are apart from each other by the distance a1 (the first both-side planar portions 21 are apart from each other by the distance a1). The first tongue piece portions 25 are provided at both end portions of each first hinge portion 15 in the axial direction (the longitudinal direction) of the first nodal ring 12. The protruding portion 35 protruding toward the inner peripheral side of the first nodal ring 12 is formed at the central part of each first tongue piece portion 25. The protruding portion 35 is formed by, e.g., burring processing.

As shown in FIG. 30 and FIG. 31B, the second nodal ring 13 includes the pair of second hinge portions 30 symmetrically provided about the central axis (the longitudinal axis) with respect to each other, and the pair of second circumferential wall portions 31 each of which is provided between the second hinge portions 30. The second hinge portion 30 includes the second central planar portion 40, and the second both-sides planar portion 41 provided on both sides of the second central planar portion 40 in the circumferential direction of the second nodal ring 13 (the bending tube 10). The second both-sides planar portions 41 each of which is provided to the corresponding second hinge portion 30 are apart from each other by the distance a2. The distance a2 is equal to the distance a1 between the first hinge portions 15 (the first both-side planar portions 21). The axial step portions 43 are formed between the second central planar portion 40 and the second both-sides planar portion 41. When the axial step portions 43 are provided, the second central planar portion 40 is arranged to the inner peripheral side than the second both-sides planar portion 41 by a distance corresponding to the wall thickness of the second nodal ring 13. The second tongue piece portions 33 are provided at both end portions of each first planar portion 40 in the axial direction (the longitudinal direction) of the second nodal ring 13. The through hole 26 is formed in the central part of each second tongue piece portion 33.

When the protruding portion 35 of each first tongue piece portion 25 engages with the through hole 26 of the corresponding second tongue piece portion 33, the first nodal ring 12 and the second nodal ring 13 are coupled with each other to allow each of them to rotate. At this time, since the distance a2 between the second both-sides planar portions 41 each of which is provided to the corresponding second hinge portion 30 is equal to the distance a1 between the first hinge portions 15 (the first both-side planar portions 21), the second both-sides planar portion 41 and the first hinge portion 15 are arranged on the same plane. The second central planar portion 20, which is arranged to the inner side than the second both-sides planar portion 41 by a distance corresponding to the wall thickness of the second nodal ring 13, is arranged to the inner peripheral side of the bending tube 10 than the first hinge portion 15 (the first central planar portion 20) by a distance corresponding to the wall thickness of each of the first nodal ring 12 and the second nodal ring 13. Therefore, in the state that the inner peripheral surface of each first central planar portion 20 is in contact with the outer peripheral surface of each second central planar portion 40 with no space therebetween, the first nodal ring 12 is coupled with the second nodal ring 13. Further, the retaining portion 39 is formed on each protruding portion 35 to prevent the through hole 26 from being disengaged from the protruding portion 35.

Figure 32:
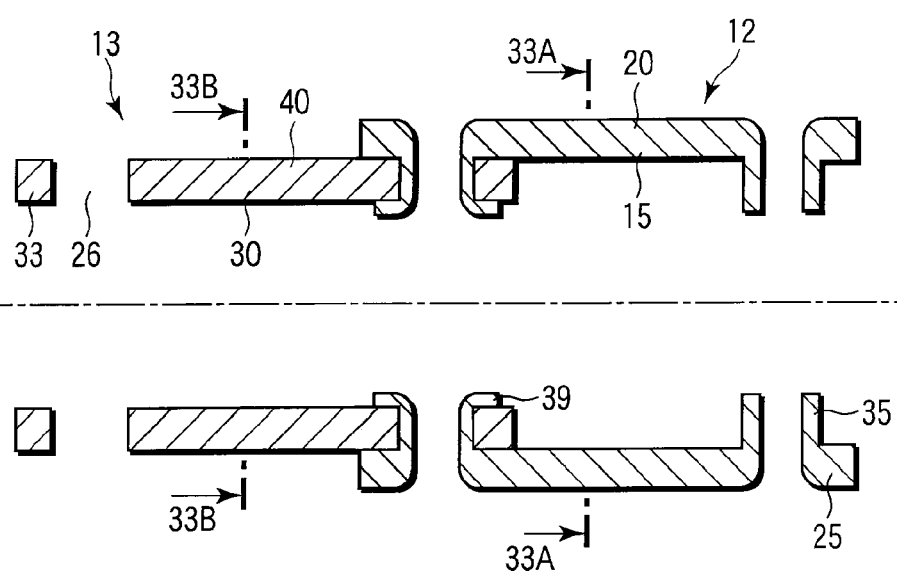
FIG. 32 is a cross-sectional view showing a first nodal ring and a second nodal ring according to a ninth modification of the first embodiment in a coupled state.

FIG. 32 is a view showing a coupled state of the first nodal and the second nodal of the ninth modification according to the first embodiment. FIG. 33A is a cross-sectional view taken along a line 33A-33A in FIG. 32, and FIG. 33B is a cross-sectional view taken along a line 33B-33B in FIG. 32. As shown in FIG. 32 and FIG. 33A, the first nodal ring 12 includes the pair of first hinge portions 15 symmetrically provided about central axis (the axis in the longitudinal direction) with respect to each other, and the pair of first circumferential wall portions 16 each of which is provided between the first hinge portions 15 and has a cylindrical surface shape. Each first hinge portion 15 includes the first central planar portion 20, and the first both-sides planar portion 21 provided on both sides of the first central planar portion 20 in the circumferential direction of the first nodal ring 12 (the bending tube 10). The first both-sides planar portion 21 each of which is provided to the corresponding first hinge portion 15 are apart from each other by the distance a1. The axial step portions (the first axial step portions) 23 are formed between the first central planar portion 20 and the first both-sides planar portion 21. A step of the axial step portion 23 is half of the wall thickness of the first nodal ring 12. When the axial step portions 23 are provided, the first central planar portion 20 is arranged to the outer peripheral side than the first both-sides planar portion 21 by a distance corresponding to half of the wall thickness of the first nodal ring 12. The first tongue piece portions 25 are provided at both end portions of each first central planar portion 20 in the axial direction (the longitudinal direction) of the first nodal ring 12. The protruding portion 35 protruding toward the inner peripheral side of the first nodal ring 12 is formed at the central part of each first tongue piece portion 25. The protruding portion 35 is formed by, e.g., burring processing.

As shown in FIG. 32 and FIG. 33B, the second nodal ring 13 includes the pair of second hinge portions 30 symmetrically provided with about the central axis (the longitudinal axis) with respect to each other, and the pair of second circumferential wall portions 31 each of which is provided between the second hinge portions 30. The second hinge portion 30 includes the second central planar portion 40, and the second both-sides planar portion 41 provided on both sides of the second central planar portion 40 in the circumferential direction of the second nodal ring 13 (the bending tube 10). The second both-sides planar portions 41 each of which is provided to the corresponding second hinge portion 30 are apart from each other by the distance a2. The distance a2 is equal to the distance a1 between the first both-sides planar portions 21. The axial step portions (the second axial step portion) 43 are formed between the second central planar portion 40 and the second both-sides planar portion 41. A step of the axial step portion 43 is half of the wall thickness of the second nodal ring 13. When the axial step portions 43 are provided, the second central planar portion 40 is arranged to the inner peripheral side than the second both-sides planar portion 41 by a distance corresponding to half of the wall thickness of the second nodal ring 13. The second tongue piece portions 33 are provided at both end portions of each second planar portion 40 in the axial direction (the longitudinal direction) of the second nodal ring 13. The through hole 26 is formed in the central part of each second tongue piece portion 33.

When the protruding portion 35 of each first tongue piece portion 25 engages with the through hole 26 of the corresponding second tongue piece portion 33, the first nodal ring 12 and the second nodal ring 13 are coupled with each other to allow each of them to rotate. At this time, since the distance a1 between the first both-sides planar portions 21 each of which is provided to the corresponding first hinge portion 15 is equal to the distance a2 between the second both-sides planar portions 41 each of which is provided to the corresponding second hinge portion 30, the first both-sides planar portion 21 and the second both-sides planar portion 41 are arranged on the same plane. Further, since the axial step portions 23 and the axial step portions 43 are provided, the first central planar portion 20 is arranged to the outer peripheral side than the first both-sides planar portion 21 by a distance corresponding to half of the wall thickness of the first nodal ring 12, and the second central planar portion 40 is arranged to the inner peripheral side than the second both-sides planar portion 41 by a distance corresponding to half of the wall thickness of the second nodal ring 13. Therefore, the second central planar portion 40 of each second hinge portion 30 is arranged to the inner peripheral side of the bending tube 10 than the first central planar portion 20 of each first hinge portion 15 by a distance corresponding to the wall thickness of each of the first nodal ring 12 and the second nodal ring 13. That is, in the state that the inner peripheral surface of each first central planar portion 20 is in contact with the outer peripheral surface of each second central planar portion 40 with no space therebetween, the first nodal ring 12 is coupled with the second nodal ring 13. Further, the retaining portion 39 is formed on each protruding portion 35 to prevent the through hole 26 from being disengaged from the protruding portion 35.

It is to be noted that the axial step portion 23 is formed in such a manner that the first central planar portion 20 is arranged to the outer peripheral side than the first both-sides planar portion 21 by a distance corresponding to half of the wall thickness of the first nodal ring 12, and the axial step portion 43 is formed in such a manner that the second central planar portion 40 of the second hinge portion 30 is arranged to the inner peripheral side than the second both-sides planar portion 41 by a distance corresponding to half of the wall thickness of the second nodal ring 13. However, it is sufficient to form the axial step portion 23 and the axial step portion 43 in such a manner that the second central planar portion 40 is arranged to the inner peripheral side of the bending tube 10 than the first central planar portion 20 by a distance corresponding to the wall thickness of each of the first nodal ring 12 and the second nodal ring 13 when the first nodal ring 12 is coupled with the third nodal ring 13.

In the above-described sixth to ninth modifications, the axial step portions 23 or 43 are provided to at least one of each first hinge portion 15 and each second hinge portion 30, whereby a step is formed between the first central planar portion 20 and the first both-sides planar portion 21 and/or between the second central planar portion 40 and the second both-side planar portion 41. In all the modifications, at least the first both-sides planar portion 21 of each first hinge portion 15 and the second both-sides planar portion 41 of each second hinge portion 30 are arranged on the same plane. Furthermore, the first central planar portion 20 of each first hinge portion 15 is arranged to the outer peripheral side than the second central planar portion 40 of each second hinge portion 30 by the distance corresponding to the wall thickness of each of the first nodal ring 12 and the second nodal ring 13. Adopting such a configuration enables the first nodal ring 12 and the second nodal ring 13 to be coupled with each other in a state that the inner peripheral surface of the first central planar portion 20 of each first hinge portion 15 is in contact with the outer peripheral surface of the second central planar portion 40 of each second hinge portion 30 with no space therebetween. The configurations of the first hinge portion 15 and the second hinge portion 30 may be modified within the scope of such a configuration.

A second embodiment according to the present invention will now be described with reference to FIG. 34. In this embodiment, the configuration of the first embodiment is modified as follows. It is to be noted that like reference numerals denote parts equal to those in the first embodiment, thereby omitting a description thereof.

Figure 34:
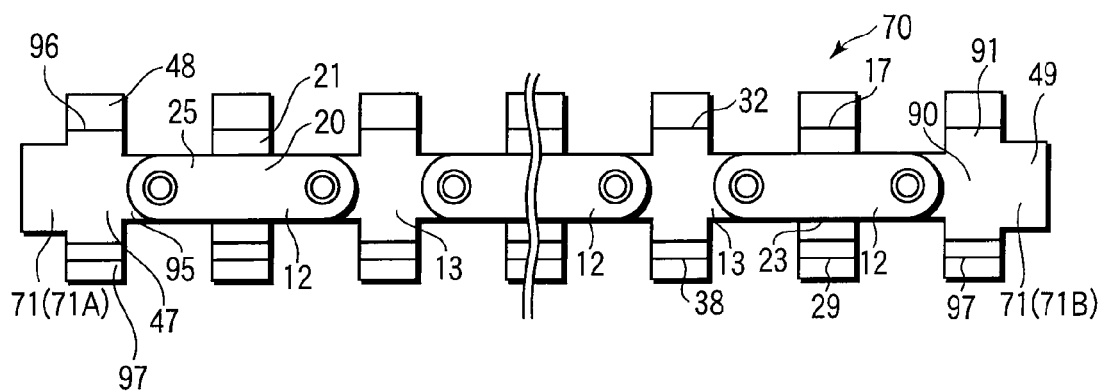
FIG. 34 is a plan view showing a bending tube according to a second embodiment of the present invention.

FIG. 34 is a view showing a configuration of a bending tube 70. As shown in FIG. 34, a both-end nodal ring 71 arranged at each of both ends of the bending tube 70 includes a pair of both-end nodal ring hinge portions 47 provided to be symmetrical about a central axis with respect to each other, and a pair of both-end nodal ring circumferential wall portions 48 each of which is provided between the both-end nodal ring hinge portions 47. A both-end nodal ring ridge line 96 is formed between the both-end hinge portion 47 and the both-end nodal ring circumferential wall portion 48. Each both-end nodal ring hinge portion 47 includes a both-end nodal ring central planar portion 90, and both-end nodal ring both-sides planar portion 91 provided on both sides of the both-end nodal ring central planar portion 90 in the circumferential direction of the both-end nodal ring 11 (the bending tube 70). The both-end nodal ring central planar portion 90 and the both-end nodal ring both-sides planar portion 91 are arranged on the same plane. That is, the both-end nodal ring hinge portion 47 has substantially the same configuration as that of the second hinge portion 30 of the second nodal ring 13 according to the first embodiment (see FIG. 3 and FIG. 5).

However, in each both-end nodal ring hinge portion 47 of the both-end nodal ring 71, both-end nodal ring tongue piece portion 95 as both-end nodal ring coupling portion is provided at one end portion alone of the both-end nodal ring central planar portion 90 in the axial direction (the longitudinal direction) of the both-end nodal ring 71. A protruding portion 35 is formed at a central part of each both-end nodal ring tongue piece portion 95. When the protruding portion 35 of each both-end nodal ring tongue piece portion 95 engages with a through hole 26 in a corresponding first tongue piece portion 25, the both-end nodal ring 71 is coupled with a first nodal ring 12. A fitting portion 49 is provided at an end portion of each both-end nodal ring hinge portion 47 on the opposite side of the side where the both-end nodal ring tongue piece portion 95 is provided in such a manner that the fitting portion 49 protrudes toward the opposite direction of the direction where the both-end nodal ring tongue piece portion 95 is arranged. A front-end nodal ring 71A is fitted to a distal-end hard portion 6 at the fitting portion 49, and a rear-end nodal ring 71B is fitted to a flexible tube 4 at the fitting portion 49.

The both-end nodal ring circumferential wall portion 48 has substantially the same configuration as that of the second circumferential wall portion 31 of the second nodal ring 13 according to the first embodiment, and it is formed into a cylindrical surface shape. However, a second wire receiver 36 is not provided in the both-end nodal ring circumferential wall portion 48. Further, like the second nodal ring 13, a both-end nodal ring joint portion 97 is formed in each both-end nodal ring 71.

It is to be noted that one of the both-end nodal rings 71 may be coupled with second tongue piece portions 33 of the second nodal ring 13 and the other may be coupled with first tongue piece portions 25 of the first nodal ring 12.

A manufacturing method of the bending tube 70 according to this embodiment will now be described.

The bending tube 70 is formed by the same manufacturing method as that used in the bending tube 10 according to the first embodiment except that both-end nodal ring preliminary bodies 71a constituting the both-end nodal rings 71 are formed in a second plate-like member 61 at the steps S105 to S108 (see FIG. 8). Moreover, when one of the both-end nodal rings 71 is coupled with the second nodal ring 13 and the other is coupled with the first nodal ring 12, the both-end nodal ring preliminary body 71a coupled with the second nodal ring 13 is formed in a first plate-like member 51 at the steps 101 to S104, and the both-end nodal ring preliminary body 71a coupled with the first nodal ring 12 is formed in a second plate-like member 61 at the steps S105 to S108.

A function of a bending portion 5 of the endoscope 1 according to this embodiment will now be described. In the bending tube 70 of the bending portion 5, if the both-end nodal ring 71 is able to be coupled with an adjacent nodal ring that is adjacent to the both-end nodal ring 71 in the longitudinal direction, it can be coupled with either the first nodal ring 12 or the second nodal ring 13. Therefore, in the bending tube 70, arrangement of the first nodal ring 12 and the second nodal ring 13 and a length of the bending tube 70 in the axial direction can be changed.

Therefore, the thus configured bending portion 5 of the endoscope 1 exhibits the following effect. That is, in the bending tube 70 of the bending portion 5 according to this embodiment, a first circumferential dimension S1 which is a sum of a length L1 of a pair of a first hinge portions 15 in the circumferential direction of the first nodal ring 12 and a circumferential length L2 of a pair of a first circumferential wall portions 16 is equal to a second circumferential dimension S2 which is a sum of a length L3 of a pair of a second hinge portions 30 in the circumferential direction of the second nodal ring 13 and a circumferential length L4 of a pair of a second circumferential wall portions 31. Further, cross-sectional shapes of the first circumferential portion 16 and a second circumferential portion 31 perpendicular to the axial direction of the bending tube 10 (which are a first cross-sectional shape and a second cross-sectional shape, respectively) are congruent with each other. Adopting such a configuration enables providing the first nodal rings 12 and the second nodal rings 13 that a distance a1 between first both-sides planar portions 21 each of which is provided to the corresponding first hinge portion 15 is equal to a distance a2 between the second hinge portions 30 (the second both-sides planar portions 41). Likewise, both-end nodal rings 71 that a distance between the both-end nodal ring both-sides planar portions 91 each of which is provided to the corresponding both-end nodal ring hinge portion 47 is equal to the distance a1 and the distance a2 are provided. Therefore, the bending tube 70 is formed without forming the both-end nodal rings 71 separately from the other nodal rings 12 and 13. As a result, workability of forming and assembling the bending tube 70 can be improved, and a manufacturing cost can be suppressed.

Moreover, each strip-like first nodal ring preliminary body 12a is coupled with each second nodal ring preliminary body 13a, and then the bending is carried out. When the first nodal ring preliminary body 12a is coupled with the second nodal ring preliminary body 13a in the tabular state, coupling strength and rotational movement characteristics between the first nodal ring 12 and the second nodal ring 13 can be assured. Likewise, coupling strength and rotational movement characteristics of the both-end nodal ring 71 and the adjacent nodal ring 12 or 13 (which is the nodal ring 12 or 13 adjacent to the both-end nodal ring 71 in the longitudinal direction in the first nodal rings 12 and the second nodal rings 13. This is the same in the following description in this embodiment) can be also assured.

Additionally, in the bending tube 70 of the bending portion 5, the distance a1 between the first both-sides planar portions 21 each of which is provided to the corresponding first hinge portion 15 is equal to the distance a2 between the second hinge portions 30 (the second both-side planar portions 41). Therefore, the first both-sides planar portion 21 of each first hinge portion 15 and the second hinge portion 30 are arranged on the same plane. At this time, the first central planar portion 20, which is arranged to the outer side than the first both-sides planar portion 21 by a distance corresponding to the wall thickness of the first nodal ring 12, is arranged to the outer peripheral side of the bending tube 10 than the second hinge portion 30 (the second central planar portion 40) by a distance corresponding to the wall thickness of each of the first nodal ring 12 and the second nodal ring 13. Therefore, in the state that the planar inner peripheral surface of each first central planar portion 20 is in contact with the planar outer peripheral surface of each second central planar portion 40 with no space therebetween, the first nodal ring 12 is coupled with the second nodal ring 13. When the planar inner peripheral surface is coupled with the planar outer peripheral surface with no space therebetween, coupling strength and rotational movement characteristics between the first nodal ring 12 and the second nodal ring 13 can be assured. Likewise, coupling strength and rotational movement characteristics between the both-end nodal ring 71 and the adjacent nodal ring 12 or 13 can also be assured.

Additionally, in the bending tube 70 of the bending portion 5, through hole 26 in each first tongue piece portion 25 of each first nodal ring preliminary body 12a is engaged with the protruding portion 35 on the corresponding second tongue piece portion 33 of the corresponding second nodal ring preliminary body 13a, and then retaining portions 39 are formed at protruding ends of the protruding portions 35 by burring expansion. Forming the retaining portions 39 enables assuring coupling strength and rotational movement characteristics between the first nodal ring and the second nodal ring 13. Likewise, coupling strength and rotational movement characteristics between the both-end nodal ring 71 and the adjacent nodal ring 12 or 13 can also be assured.

Further, in the bending tube 70 of the bending portion 5, if the both-end nodal ring 71 is able to be coupled with the nodal ring adjacent to the both-end nodal ring 71 in the longitudinal direction, the both-end nodal ring 71 can be coupled with either the first nodal ring 12 or the second nodal ring 13. Therefore, in the bending tube 70, arrangement of the first nodal rings 12 and the second nodal rings 13 and a length of the bending tube 70 can be changed. As a result, it is possible to provide the bending tube 70 that is not structurally restricted by a length of the bending portion 5, built-in components, and others.

A third embodiment according to the present invention will now be described with reference to FIG. 35 and FIG. 36A. In this embodiment, the configuration of the first embodiment is modified as follows. It is to be noted that like reference numerals denote parts equal to those in the first embodiment, thereby omitting a description thereof.

Figure 35:
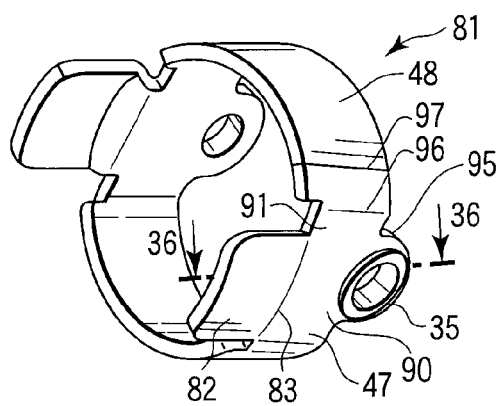
FIG. 35 is a perspective view showing a both-end nodal ring according to a third embodiment of the present invention.
Figure 36A:
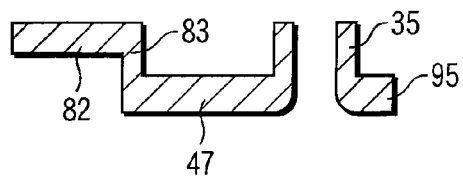
FIG. 36A is a cross-sectional view taken along a line 36-36 in FIG. 35.

FIG. 35 is a view showing a configuration of a both-end nodal ring 81 according to this embodiment. As shown in FIG. 35, the both-end nodal ring 81 arranged at each of both ends of a bending tube includes a pair of both-end nodal ring hinge portions 47 provided to be symmetrical about a central axis with respect to each other, and a pair of both-end nodal ring circumferential wall portions 48 each of which is provided between the both-end nodal ring hinge portions 47. A both-end nodal ring ridge line 96 is formed between the both-end hinge portion 47 and the both-end nodal ring circumferential wall portion 48. The both-end nodal ring hinge portion 47 includes a both-end nodal ring central planar portion 90, and both-end nodal ring both-sides planar portion 91 provided on both sides of the both-end nodal ring central planar portion 90 in the circumferential direction of the both-end nodal ring 11 (the bending tube 10). The both-end nodal ring central planar portion 90 and the both-end nodal ring both-sides planar portion 91 are arranged on the same plane. That is, the both-end nodal ring hinge portion 47 has substantially the same configuration as that of the second hinge portion 30 of the second nodal ring 13 according to the first embodiment (see FIG. 3 and FIG. 5).

However, in each both-end nodal ring hinge portion 47 of the both-end nodal ring 81, a both-end nodal ring tongue piece portion 95 as a both-end nodal ring coupling portion is provided at one end portion alone of the both-end nodal ring central planar portion 90 in the axial direction (the longitudinal direction) of the both-end nodal ring 81. A protruding portion 35 is formed in a central part of each both-end nodal ring tongue piece portion 95. When the protruding portion 35 of each both-end nodal ring tongue piece portion 95 engages with a through hole 26 in a corresponding first tongue piece portion 25, the both-end nodal ring 81 is coupled with a first nodal ring 12. The both-end nodal ring circumferential wall portion 48 has substantially the same configuration as that of the second circumferential wall portion 31 of the second nodal ring 13 according to the first embodiment, and it is formed into a cylindrical surface shape. However, a second wire receiver 36 is not provided in the both-end nodal ring circumferential wall portion 48. Further, like the second nodal ring 13, a both-end nodal ring joint portion 97 is formed in the both-end nodal ring 71.

On a side of the both-end nodal ring hinge portions 47 opposite to a side where the both-end nodal ring tongue piece portions 95 are arranged, a pair of fitting portions (protruding fitting portions) 82 are provided to protrude in the opposite direction of the direction where the both-end nodal ring tongue piece portions 95 are arranged. The fitting portions 82 are arranged to be apart from each other at substantially 180° in the circumferential direction of the both-end nodal ring 81. A front-end nodal ring 81A is fitted to a distal-end hard portion 6 at the fitting portions 82, and a rear-end nodal ring 81B is fitted to a flexible tube 4 at the fitting portions 82. FIG. 36A is a cross-sectional view taken along a line 36A-36A in FIG. 35. As shown in FIG. 35 and FIG. 36A, a fitting step portion (a circumferential fitting step portion) 83 is formed between each both-end nodal ring hinge portion 47 and each fitting portion 82 along the circumferential direction of the both-end nodal ring 81. When the fitting step portion 83 is provided, the fitting portion 82 is arranged to the outer peripheral side of the both-end nodal ring 81 than the both-end nodal ring hinge portion 47 by a distance corresponding to a step of the fitting step portion 83.

It is to be noted that each both-end nodal ring hinge portion 47 of the both-end nodal ring 81 has substantially the same configuration as that of the first hinge portion 15 (see FIG. 3 and FIG. 4) according to the first embodiment, and an axial step portion 93 may be formed between the both-end nodal ring central planar portion 90 and the both-end nodal ring both-sides planar portion 91. In this case, the fitting step portion 83 is provided between each both-end nodal ring central planar portion 90 and each fitting portion 82.

A function of the bending portion 5 in the endoscope 1 according to this embodiment will now be described.

In the bending tube 10 of the bending portion 5, the fitting step portion 83 is formed between each both-end nodal ring hinge portion 47 of the both-end nodal ring 81 and each fitting portion 82. When the fitting step portion 83 is provided, the front-end nodal ring 81A can be easily fitted to the distal-end hard portion 6, and a rear-end nodal ring 81B can be easily fitted to the flexible tube 4.

Therefore, the thus configured bending portion 5 of the endoscope 1 exhibits the following effect. That is, in the bending tube 10 of the bending portion 5 according to this embodiment, a first circumferential dimension S1 which is a sum of a length L1 of a pair of a first hinge portions 15 in the circumferential direction of the first nodal ring 12 and a circumferential length L2 of a pair of a first circumferential wall portions 16 is equal to a second circumferential dimension S2 which is a sum of a length L3 of a pair of a second hinge portions 30 in the circumferential direction of the second nodal ring 13 and a circumferential length L4 of a pair of a second circumferential portions 31. Further, cross-sectional shapes of the first circumferential portion 16 and a second circumferential portion 31 perpendicular to the axial direction of the bending tube 10 (which are a first cross-sectional shape and a second cross-sectional shape, respectively) are congruent with each other. Adopting such a configuration enables providing the first nodal rings 12 and the second nodal rings 13 that a distance a1 between first both-sides planar portions 21 each of which is provided to the corresponding first hinge portion 15 is equal to a distance a2 between the second hinge portions 30 (the second both-sides planar portions 41). Likewise, both-end nodal rings 81 that a distance between the both-end nodal ring both-sides planar portions 91 each of which is provided to the corresponding both-end nodal ring hinge portion 47 is equal to the distance a1 and the distance a2 can be provided. Therefore, the bending tube is formed without forming the both-end nodal rings 81 separately from the other nodal rings 12 and 13. As a result, workability of forming and assembling the bending tube 10 can be improved, and a manufacturing cost can be suppressed.

Moreover, each strip-like first nodal ring preliminary body 12a is coupled with each strip-like second nodal ring preliminary body 13a, and then the bending is carried out. When the first nodal ring preliminary body 12a is coupled with the second nodal ring preliminary body 13a in the tabular state, coupling strength and rotational movement characteristics between the first nodal ring 12 and the second nodal ring 13 can be assured. Likewise, coupling strength and rotational movement characteristics of the both-end nodal ring 81 and the adjacent nodal ring 12 or 13 (which is the nodal ring 12 or 13 adjacent to the both-end nodal ring 81 in the longitudinal direction in the first nodal rings 12 and the second nodal rings 13. This is the same in the following description in this embodiment) can be also assured.

Additionally, in the bending tube of the bending portion, since the distance a1 between the first both-sides planar portions 21 each of which is provided to the corresponding first hinge portion 15 is equal to the distance a2 between the second hinge portions 30 (the second both-side planar portions 41), the first both-sides planar portion 21 of each first hinge portion 15 and the second hinge portion 30 are arranged on the same plane. At this time, the first central planar portion 20, which is arranged to the outer side than the first both-sides planar portion 21 by a distance corresponding to the wall thickness of the first nodal ring, is arranged to the outer peripheral side of the bending tube 10 than the second hinge portion 30 (the second central planar portion 40) by a distance corresponding to the wall thickness of each of the first nodal ring 12 and the second nodal ring 13. Therefore, in the state that the planar inner peripheral surface of each first central planar portion 20 is in contact with the planar outer peripheral surface of each second central planar portion 40 with no space therebetween, the first nodal ring 12 is coupled with the second nodal ring 13. When the planar inner peripheral surface is coupled with the planar outer peripheral surface with no space therebetween, coupling strength and rotational movement characteristics between the first nodal ring 12 and the second nodal ring 13 can be assured. Likewise, coupling strength and rotational movement characteristics between the both-end nodal ring 81 and the adjacent nodal ring 12 or 13 can be also assured.

Additionally, in the bending tube of the bending portion, through hole 26 in each first tongue piece portion 25 of each first nodal ring preliminary body 12a is engaged with the protruding portion 35 on the corresponding second tongue piece portion 33 of the corresponding second nodal ring preliminary body 13a, and then retaining portions 39 are formed at protruding ends of the protruding portions 35 by burring expansion. Forming the retaining portions 39 enables assuring coupling strength and rotational movement characteristics between the first nodal ring 12 and the second nodal ring 13. Likewise, coupling strength and rotational movement characteristics between the both-end nodal ring 81 and the adjacent nodal ring 12 or 13 can also be assured.

Further, in the bending tube of the bending portion, the fitting step portion 83 is formed between each both-end nodal ring hinge portion 47 of the both-end nodal ring 81 and each fitting portion 82. When the fitting step portion 83 is provided, the front-end nodal ring 81A can be easily fitted to the distal-end hard portion 6, and the rear-end nodal ring 81B can be easily fitted to the flexible tube 4. As a result, workability of forming and assembling the bending tube 10 can be improved.

A fourth embodiment according to the present invention will now be described with reference to FIG. 36B. In this embodiment, the configuration of the first embodiment is modified as follows. It is to be noted that like reference numerals denote parts equal to those in the first embodiment, thereby omitting a description thereof.

Figure 36B:
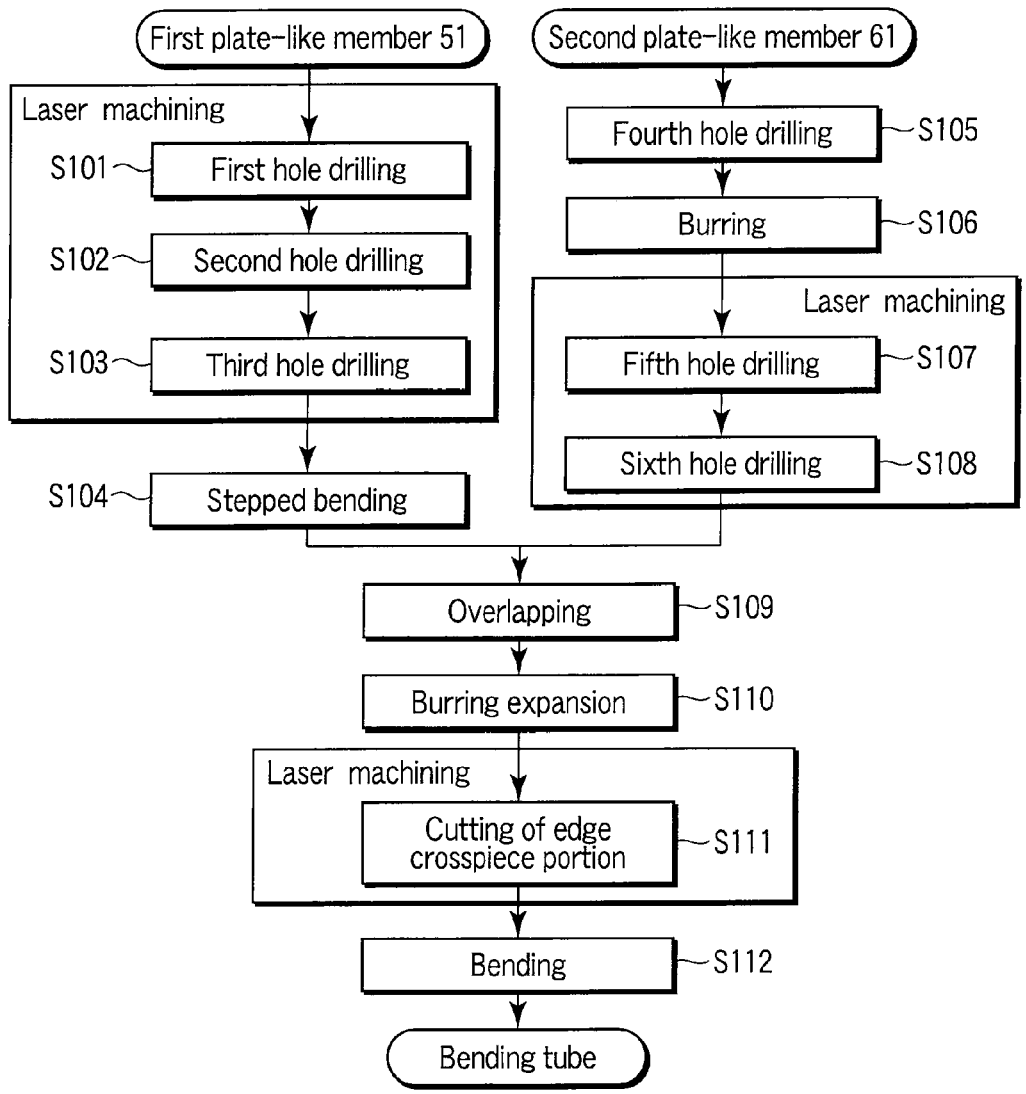
FIG. 36B is a flowchart showing a manufacturing method of a bending tube according to a fourth embodiment of the present invention.

FIG. 36B is a view showing a manufacturing method of the bending tube 10 according to this embodiment. As shown in FIG. 36B, in the bending tube 10 according to this embodiment, laser machining is used to carry out first hole drilling S101 of forming through hole 26 of each first tongue piece portion 25 of first nodal ring 12 in a first plate-like member 51, second hole drilling S102 of forming first wire receiver preliminary portions 28a, and third hole drilling S103 of forming first nodal preliminary bodies 12a and both-end preliminary bodies 11a. Furthermore, laser machining is also used to carry out fifth hole drilling S107 of forming second wire receiver preliminary portions 36a of second nodal rings 13 in a second plate-like member 61 and sixth hole drilling S108 of forming second nodal ring preliminary bodies 13a. Moreover, edge crosspiece portion cutting S111 of cutting a first edge crosspiece portion 58 in the first plate-like member 51 and a second edge crosspiece portion 68 in the second plate-like member 61 is also performed by the laser machining.

A function of the bending portion 5 of the endoscope 1 according to this embodiment will now be described.

In the bending tube 10 of the bending portion 5 according to this embodiment, the laser machining is used to carry out the first hole drilling S101, the second hole drilling S102, the third hole drilling S103, the fifth hole drilling S107, the sixth hole drilling S108, and the edge crosspiece portion cutting S111. Since a die is not used in these steps, a cost of the die is not required, thereby reducing a manufacturing cost.

Therefore, the thus configured bending portion 5 of the endoscope 1 exhibits the following effect. That is, in the bending tube 10 of the bending portion 5 according to this embodiment, a first circumferential dimension S1 which is a sum of a length L1 of a pair of a first hinge portions 15 in the circumferential direction of the first nodal ring 12 and a circumferential length L2 of a pair of a first circumferential wall portions 16 is equal to a second circumferential dimension S2 which is a sum of a length L3 of a pair of a second hinge portions 30 in the circumferential direction of the second nodal ring 13 and a circumferential length L4 of a pair of a second circumferential portions 31. Further, cross-sectional shapes of the first circumferential portion 16 and a second circumferential portion 31 perpendicular to the axial direction of the bending tube 10 (which are a first cross-sectional shape and a second cross-sectional shape, respectively) are congruent with each other. Adopting such a configuration enables providing the first nodal rings 12 and the second nodal rings 13 that a distance a1 between first both-sides planar portions 21 each of which is provided to the corresponding first hinge portion 15 is equal to a distance a2 between the second hinge portions 30 (the second both-sides planar portions 41). Likewise, both-end nodal rings 11 that a distance between both-end nodal ring both-sides planar portions 91 each of which is provided to the corresponding both-end nodal ring hinge portion 47 is equal to the distance a1 and the distance a2 can be provided. Therefore, the bending tube 10 is formed without forming the both-end nodal rings 11 separately from the other nodal rings 12 and 13. As a result, workability of forming and assembling the bending tube 70 can be improved, and a manufacturing cost can be suppressed.

Moreover, each strip-like first nodal ring preliminary body 12a is coupled with each strip-like second nodal ring preliminary body 13a, and then the bending is carried out. When the first nodal ring preliminary body 12a is coupled with the second nodal ring preliminary body 13a in the tabular state, coupling strength and rotational movement characteristics between the first nodal ring 12 and the second nodal ring 13 can be assured. Likewise, coupling strength and rotational movement characteristics of the both-end nodal ring 11 and the nodal ring 13 can also be assured.

Additionally, in the bending tube of the bending portion, the distance a1 between the first both-sides planar portions 21 each of which is provided to the corresponding first hinge portion 15 is equal to the distance a2 between the second hinge portions 30 (the second both-side planar portions 41). Therefore, the first both-sides planar portion 21 of each first hinge portion 15 and the second hinge portion 30 are arranged on the same plane. At this time, the first central planar portion 20, which is arranged to the outer side than the first both-sides planar portion 21 by a distance corresponding to the wall thickness of the first nodal ring, is arranged to the outer peripheral side of the bending tube 10 than the second hinge portion 30 (the second central planar portion 40) by a distance corresponding to the wall thickness of each of the first nodal ring 12 and the second nodal ring 13. Therefore, in the state that the planar inner peripheral surface of each first central planar portion 20 is in contact with the planar outer peripheral surface of each second central planar portion 40 with no space therebetween, the first nodal ring 12 is coupled with the second nodal ring 13. When the planar inner peripheral surface is coupled with the planar outer peripheral surface with no space therebetween, coupling strength and rotational movement characteristics between the first nodal ring 12 and the second nodal ring 13 can be assured. Likewise, coupling strength and rotational movement characteristics between the both-end nodal ring 11 and the second nodal ring 13 can also be assured.

Additionally, in the bending tube of the bending portion, through hole 26 in each first tongue piece portion 25 of each first nodal ring preliminary body 12a is engaged with the protruding portion 35 in the corresponding second tongue piece portion 33 of the corresponding second nodal ring preliminary body 13a, and then retaining portions 39 are formed at protruding ends of the protruding portions 35 by burring expansion. Forming the retaining portions 39 enables assuring coupling strength and rotational movement characteristics between the first nodal ring 12 and the second nodal ring 13. Likewise, coupling strength and rotational movement characteristics between the both-end nodal ring 11 and the second nodal ring 13 can be also assured.

Further, in the bending tube of the bending portion, the laser machining is used to carry out the first hole drilling S101, the second hole drilling S102, the third hole drilling S103, the fifth hole drilling S107, and the sixth hole drilling S108. Since a die is not used in these steps, a cost of the die is not required, and a manufacturing cost can be reduced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A manufacturing method of a bending tube in which two types of nodal rings, which are first nodal rings and second nodal rings, are alternately coupled with each other in a longitudinal direction to allow each of them to rotate, the method comprising:

forming a predetermined number of first nodal-ring preliminary bodies in a first plate-like member, each of the first nodal-ring preliminary bodies having a strip-like shape and being configured to be formed into a corresponding one of the first nodal rings by circularizing, one or both ends each first nodal ring preliminary body in a circumferential direction of the bending tube being coupled with an edge of the first plate-like member through a first edge crosspiece portion in the first plate-like member, and first gaps being formed between the first nodal ring preliminary bodies in the longitudinal direction in the first plate-like member;

forming a predetermined number of second nodal-ring preliminary bodies in a second plate-like member, the second plate-like member being different from the first plate-like member and being a separate member from the first plate-like member, each of the second nodal ring preliminary bodies having a strip-like shape and being configured to be formed into a corresponding one of the second nodal rings by circularizing, one or both ends each second nodal ring preliminary body in a circumferential direction being coupled with an edge of the second plate-like member through a second edge crosspiece portion in the second plate-like member, and second gaps being formed between the second nodal ring preliminary bodies in the longitudinal direction in the second plate-like member;

forming a protruding portion on one of a first coupling portion provided to each first nodal ring preliminary body and a second coupling portion provided to each second nodal ring preliminary body by burring processing;

forming a through hole, which engages with the protruding portion, in the other of each first coupling portion and each second coupling portion;

overlapping the first plate-like member with the second plate-like member in a state that each of the second nodal ring preliminary bodies is arranged in a corresponding one of the first gaps of the first plate-like member and each of the first nodal ring preliminary bodies is arranged in a corresponding one of the second gaps of the second plate-like member, and thereby engaging the protruding portions with the through holes and coupling the first nodal ring preliminary bodies with the second nodal ring preliminary bodies;

disconnecting the first nodal ring preliminary bodies from the edge of the first plate-like member at the first edge crosspiece portion and disconnecting the second nodal ring preliminary bodies from the edge of the second plate-like member at the second edge crosspiece portion; and forming the first nodal ring preliminary bodies and the second nodal ring preliminary bodies into circular shapes by bending processing after coupling the first nodal ring preliminary bodies with the second nodal ring preliminary bodies, and joining and connecting part or all of both ends of each first nodal ring preliminary body in the circumferential direction and joining and connecting part or all of both ends of each second nodal ring preliminary body in the circumferential direction.

2. The manufacturing method according to claim 1, further comprising:
forming both-end nodal rings which comprise a front-end nodal ring provided at a most distal end side of the bending tube and coupled with a distal-end hard portion, and a rear- end nodal ring provided at the most proximal end side of the bending tube and coupled with a flexible tube, and each of which includes a both-end nodal ring coupling portion coupled with a longitudinally adjacent nodal ring which is one of the the first nodal rings or the second nodal rings,
wherein the forming the both-end nodal rings includes:
forming both-end nodal ring preliminary bodies in the first plate-like member or the second plate-lie member, each of the both-end nodal ring preliminary bodies having a strip-like shape and being configured to be formed into a corresponding one of the both-end nodal rings by circularizing, an end portion of each of the both-end nodal ring preliminary bodies on a side opposite from a side where the both-end nodal ring coupling portion is provided being coupled with the edge of the first plate-like member or the second plate-like member through a both-end edge crosspiece portion, and gaps being provided between the both-end nodal ring preliminary bodies and adjacent ones of the first nodal ring preliminary bodies or the second nodal ring preliminary bodies;
forming in each both-end nodal ring coupling portion a protruding portion to engage with the through hole formed in one of the first or second coupling portions, or a through hole to engage with the protruding portion formed in one of the first or second coupling portions;
after overlapping the first plate-like member and the second plate-like member, coupling each of the both-end nodal ring preliminary bodies to a longitudinally adjacent nodal ring preliminary body of the first nodal ring preliminary bodies or the second nodal ring preliminary bodies; and
forming each both-end nodal ring preliminary body into a circular shape by bending processing and joining and connecting part or all of both ends of each both-end nodal ring preliminary body in the circumferential direction.

3. The manufacturing method according to claim 1, further comprising:
forming in each first nodal ring preliminary body first hinge portion preliminary portions constituting a pair of first hinge portions each of which includes a first central planar portion including the first coupling portion and a first both-sides planar portion provided on both sides of the first central planar portion in the circumferential direction and which are arranged to be symmetrical about a longitudinal axis with respect to each other in the first nodal ring;
forming in each second nodal ring preliminary body second hinge portion preliminary portions constituting a pair of second hinge portions each of which includes a second central planar portion including the second coupling portion and a second both-sides planar portion provided on both sides of the second central planar portion in the circumferential direction and arranged on the same plane as the first both-sides planar portion of each of the first hinge portion preliminary portion, and which are arranged to be symmetrical about a longitudinal axis with respect to each other in the second nodal ring; and
forming in at least one of each first hinge portion preliminary portion and each second hinge portion preliminary portion an axial step portion, which allows the first central planar portion to be arranged to an outer peripheral side of the bending tube with respect to the second central planar portion by a distance corresponding to a wall thickness of the nodal ring after forming each first nodal ring preliminary body and each second nodal ring preliminary body into the circular shape, between the first central planar portion and the first both-side planar portion over the entire length of the first nodal ring preliminary body in the longitudinal direction and/or between the second central planar portion and the second both-side planar portion over the entire length of the second nodal ring preliminary body in the longitudinal direction.

4. The manufacturing method according to claim 1,
wherein the forming each first nodal ring preliminary body includes forming the first nodal ring preliminary body in the first plate-like member by press work using a die,
the forming each second nodal ring preliminary body includes forming the second nodal ring preliminary body in the second plate-like member by press work using a die,
the forming each protruding portion includes forming the protruding portion in one of each first coupling portion and each second coupling portion by press work using a die,
the forming each through hole includes forming the through hole in the other of each first coupling portion and each second coupling portion by press work using a die,
the coupling each first nodal ring preliminary body with each second nodal ring preliminary body includes coupling the first nodal ring preliminary body with the second nodal ring preliminary body by press work using a die,
the disconnecting each first nodal ring preliminary body from the edge of the first plate-like member and the disconnecting each second nodal ring preliminary body from the edge of the second plate-like member includes disconnecting the first nodal ring preliminary body from the edge of the first plate-like member at the first edge crosspiece portion and disconnecting the second nodal ring preliminary body from the edge of the second plate-like member at the second edge crosspiece portion by press work using a die, and
the forming each first nodal ring preliminary body and each second nodal ring preliminary body into circular shapes includes forming each first nodal ring preliminary body and each second nodal ring preliminary body into the circular shapes by press work using a die.

5. The method according to claim 1,
wherein the forming each first nodal ring preliminary body includes forming the first nodal ring preliminary body in the first plate-like member by laser machining,
the forming each second nodal ring preliminary body includes forming the second nodal ring preliminary body in the second plate-like member by laser machining,
the forming each through hole includes forming the through hole in each first coupling portion or each second coupling portion by laser machining, and
the disconnecting each first nodal ring preliminary body from the edge of the first plate-like member and the disconnecting each second nodal ring preliminary body from the edge of the second plate-like member includes disconnecting the first nodal ring preliminary body from the edge of the first plate-like member at the first edge crosspiece portion and disconnecting the second nodal ring preliminary body from the edge of the second plate-like member at the second edge crosspiece portion by laser machining.

6. The manufacturing method according to claim 1, further comprising forming a retaining portion, whose diameter is expanded beyond a diameter of the through hole, at a protruding end of each protruding portion.

* * * * *